US006797492B2

(12) United States Patent
Daugherty et al.

(10) Patent No.: US 6,797,492 B2
(45) Date of Patent: Sep. 28, 2004

(54) METHOD FOR REDUCING THE IMMUNOGENICITY OF ANTIBODY VARIABLE DOMAINS

(75) Inventors: Bruce L. Daugherty, South Orange, NJ (US); George E. Mark, III, Princeton Junction, NJ (US); Eduardo A. Padlan, Kensington, MD (US)

(73) Assignees: Merck & Co., Inc., Rahway, NJ (US); United States of America, Washington, DC (US)

( * ) Notice: Subject to any disclaimer, the term of this patent is extended or adjusted under 35 U.S.C. 154(b) by 0 days.

(21) Appl. No.: 09/810,502

(22) Filed: Mar. 16, 2001

(65) Prior Publication Data

US 2002/0034765 A1 Mar. 21, 2002

Related U.S. Application Data

(63) Continuation of application No. 08/905,280, filed on Aug. 1, 1997, now abandoned, which is a continuation of application No. 08/609,218, filed on Mar. 1, 1996, now abandoned, which is a continuation of application No. 08/109,187, filed on Aug. 19, 1993, now abandoned, which is a continuation-in-part of application No. 07/702,217, filed on May 17, 1991, now abandoned.

(51) Int. Cl.[7] .............................................. C12N 15/00
(52) U.S. Cl. ................. 435/69.6; 530/387.1; 530/387.3
(58) Field of Search ........................... 530/387.1, 387.3; 435/69.6, 70.21; 424/130.1, 133.1

(56) References Cited

U.S. PATENT DOCUMENTS 4,816,567 A 3/1989 Cabilly et al.

FOREIGN PATENT DOCUMENTS

| | | |
|---|---|---|
| EP | 239400 | 9/1987 |
| EP | 255694 | 2/1988 |
| EP | 274394 | 7/1988 |
| EP | 328404 | 6/1989 |
| EP | 323806 | 7/1989 |
| EP | 327000 | 8/1989 |
| EP | 332424 | 9/1989 |
| EP | 434257 | 6/1991 |
| EP | 438312 | 7/1991 |
| GB | 2 188 638 | 10/1987 |
| WO | WO 87/02671 | 5/1987 |
| WO | WO 89/00999 | 2/1989 |
| WO | WO 91/08298 | 6/1991 |
| WO | WO 91/09967 | 7/1991 |
| WO | WO 91/10742 | 7/1991 |
| WO | WO 91/11198 | 8/1991 |
| WO | WO 91/11534 | 8/1991 |

OTHER PUBLICATIONS

Novotny et al., PNAS 83:226–30, 1986.*
Hunter, W.M. et al., Preparation of Iodine–131 Labelled Human Growth Hormone of High Specific Activity, 1962, Nature, 194, pp. 495–496 (cumulative).

English, D. et al., Single Separation of Red Blood Cells: Granulocytes and Mononuclear Leukocytes on Discontinuous Density Gradents of Ficoll–Hypaque, 1974, J. Immunological Methods, 5, pp. 249–252 (cumulative).

Bernstein, F.C. et al., The Protein Data Bank: A Computer–based Archival File for Macromolecular Structures, 1977, J. Mol. Biol., 112, pp. 535–542 (cumulative).

Rodbard, D. et al., Improved Curve–Fitting, Parallelism Testing, Characterization Of Sensitivity And Specificity, Validation, And Optimization For Radioligand Assays, 1978, In: Radioimmunoassay & Related Procedures In Medicine, International Atomic Agency, Vienna, vol. 1, pp. 469–504 (cumulative).

Chirgwin, J. et al., Isolation of Biologically Active Ribonucleic Acid from Sources Enriched in Ribonuclease, 1979, Biochemistry, 18, pp. 5294–5299 (cumulative).

Flanagan, J.G. et al., Arrangement of human immnoglobulin heavy chain constant region genes implies evolutionary duplication of a segment containing γ, ε and α genes, 1982, Nature, 300, pp. 709–813 (cumulative).

Daugherty, B.L et al.,Polymerase chain reaction facilitates the cloning, CDR–grafting and rapid expression of a murine monoclonal antibody directed against the CD18 component of leukocyte integrins, 1991, Nucleic Acids Research, 19, pp. 2471–2476 (cumulative).

Beatty, P.G. et al., Definition of a Common Leukocyte Cell–Surface Antigen )Lo95–150) Associated with Diverse Cell–Mediated Immune Functions, 1983, J. Immunol., 131, pp. 2913–1918 (cumulative).

Sanchez–Madrid, F. et al., A Human Leukocyte Differentiation Antigen Family With Distinct α–Subunits and a Common B–Subunit, 1983, J. Exp. Med. 158, pp. 1785–1803 (cumulative).

VanVoorhis, W.C. et al., Specific Antimononuclear Phagocyte Monoclonal Antibodies, 1983, J. Exp. Med., 158, pp. 126–145 (cumulative).

Wright, S.D. et al., Identification of the C3bi receptor of human monocytes and macrophages by using monoclonal antibodies (cumulative).

Gritz, L et al., Plasmid–encoded hygromycin B resistance: the sequence of hygromycin B phosphotransferase gene and its expression in *Escherichia coli* and *Saccharomyces cerevisiae*, 1983, Gene, 25, pp. 179–188 (cumulative).

(List continued on next page.)

*Primary Examiner*—Larry R. Helms
(74) *Attorney, Agent, or Firm*—Yang Xu; Jack L. Tribble

(57) ABSTRACT

A unique method is disclosed for identifying and replacing immunoglobulin surface amino acid residues which converts the antigenicity of a first mammalian species to that of a second mammalian species. The method will simultaneously change immunogenicity and strictly preserve ligind binding properties. The judicious replacement of exterior amino acid residues has no effect on the ligind binding properties but greatly alters immunogenicity.

3 Claims, 24 Drawing Sheets

OTHER PUBLICATIONS

Berkner, K.L. et al., Effect of the tripartite leader on synthesis of a non–viral protein in an adenovirus 5 recombinant, 1985, Nucleic Acids, Res., 13, pp. 841–857 (cumulative).

Riechmann, L. et al., Reshaping human antibodies for therapy, 1988, Nature, 332, pp. 323–327 (cumulative).

LoBuglio, A.F. et al., Mouse/human chimeric monoclonal antibody in man: Kinetics and immune response, 1989, Proc. Nat'l Acad. Sci. USA, 86, pp. 4220–4224 (cumulative).

Sheriff, S., Antibody–Antigen Complexes1, 1990, Annu. Rev. Biochem., 59, pp. 439–473 (cumulative).

Padan, E., On the Nature of Antibody Combining Sites: Unusual Structural Features That May Confer on These Sites an Enhanced Capacity for Binding Ligands, 1990, Proteins: Struc., Funct., Genet., 7, pp. 112–124 (cumulative).

Hakimi, J. et al., Reduce Immunogenicity And Improved Pharmacokinetics Of Humanized Anti–Tac In Cynomolgus Monkeys, 1991, J. Immunol., 147, pp. 1352–1359 (cumulative).

Lo, S.K. et al., Transient Adhesion of Neutrophils To Endothelium, J. Exp. Med., 169, pp. 1779–1793 (cumulative).

Sequences of Proteins of Immunol. Int., 4th Edition, U.S. Dept. of Health and Human Services (cumulative).

Gorman, S.D. et al., Reshaping a therapeutic CD4 antibody, 1991, Proc. Nat'l. Acad. Sci., 88, pp. 4181–4185 (cumulative).

Padlan, E. et al., Modeling of Antibody Comining Sites, 1991, Methods in Enzymology, 203, pp. 30–21 (cumulative).

Padlan, E., A Possible Procedure for Reducing The Immunogenicity of Antibody Variable Domains While Preserving Their Ligand–Binding Properties, 1991, Molec. Immun., 28(4/5), pp. 489–498 (cumulative).

Verhoeyen, M. et al., Reshaping Human Antibodies: Grafting an Antilysozme Activity, 1988, Science, 239, pp. 1534–1536 (cumulative).

Queen, C. et al., A humanized antibody that binds to the interleukin 2 receptor, 1989, PNAS, 86, pp. 10029–10033 (cumulative).

Bolger, M.B., et al., Computer Modeling of Combining Site Structure of Anti–hapten Monoclonal Antibodies, 1991, Methods in Enzy., 203, pp. 21–45 (cumulative).

Lewin, 'When Does Homology Mean Something else', Science 237: 1570 (1987).

Reeck et al. 'Homology in Proteins and Nucleic Acids . . . out of it', Cell, vol. 50, p 667, 1987.

Creighton Proteins Structure and Molecular Principals, WH Freeman & Co.NY pp 93–94, 1983.

Creighton, 'Experimental Studies of Protein Folding and Unfolding', Biophys. Mole/Bio, vol. 33, pp 231–233, 1975.

Burgess et al. 'Possible Dissociation of the Heparin–binding . . . by Site directed Mutagenesis of a Single Lysine Residue', J. of Cell Biol., vol. 111, pp 2129–2138, 1990.

Lazar et al. Transofrming Growht Factor alpha: Mutation . . . Different . . . Biological Activities', Mol Cell Biol. vol. 8 B(3), pp 1247–1252, 1988.

Schwartz et al. 'A superactive insulin [B10–Aspartic acid] insulin(human)', Proc. Natl. Acad. Sci. USA, Vo.1, 84, pp. 6408–6411, 1987.

Lin et al. 'Structure Function Relationships in Glucagon: . . . (homoserine lactone 27)–glucagon', Biochemistry, vol. 14, pp 1559–1563 1975.

Rudikoff et al. 'Functional antibody lacing a variable region disulfide bridge', Proc. Natl. acad. Sci, USA, vol. 79, p 1979, 1982.

Panka et al. 'Variable region framework differences . . . antibodies', Proc. Natl.. Acad. Sci, USA, vol. 85, pp 3080–3084, 1988.

Amit et al. 'Three Dimensional Structure of an Antigen–Antibody Complex at 2.8A Resolution', Science, vol. 233, p 747,753, 1986.

Ehrlich et al. PCT Technology, Macmillan Publishers, pp 80–83, 1989.

Paul, Fundamntal Immunology p 242, Third Edition 1993.

Hunter et al., "Preparation of Iodine–131 Labeled Human Growth Hormone of High Specific Activity" 1962, Nature vol. 194, pp. 495–6.

English et al., "Single Step Separation of Red Blood Cells, Granulocytes and Mononuclear Leukocytes on Discontinuous Density Gradients of Ficoll–Hypaque" 1974 J. Immunological Methods 5, pp. 349–252.

Bernstein et al., "The Protein Data Bank: A Computer–based Archival File for Macromolecular Structures" 1997 J Mol Biol, 112, pp. 535–542.

* cited by examiner

|  | Fractional Accessibility | | | | Residues In Subgroup | | |
|---|---|---|---|---|---|---|---|
| Position | KOL | | J539 | | I | II | III |
|  | Residue | Exposure | Residue | Exposure |  |  |  |
| 1 | E | 1.00 Ex | E | 1.00 Ex | Q | Q | E |
| 2 | V | 0.23 mB | V | 0.37 mB | V | V | V M |
| 3 | Q | 0.82 Ex | K | 0.82 Ex | Q | T Q | Q |
| 4 | L | 0.00 Bu | L | 0.10 Bu | L | L | L |
| 5 | V | 0.87 Ex | L | 1.00 Ex | V | R Q K T | V L |
| 6 | Q | 0.00 Bu | E | 0.09 Bu | Q | E | E |
| 7 | S | 0.94 Ex | S | 0.94 Ex | S | S | S |
| 8 | G | 1.00 Ex | G | 1.00 Ex | G | G | G |
| 9 | G | 0.00 Bu | G | 0.00 Bu | A | P | G |
| 10 | G | 1.00 Ex | G | 1.00 Ex | E | A G T | G A |
| 11 | V | 0.90 Ex | L | 0.81 Ex | V | L | L F |
| 12 | V | 0.25 mB | V | 0.25 mB | K | V | V |
| 13 | Q | 0.71 mE | Q | 0.87 Ex | K | K | Q |
| 14 | P | 0.59 PB | P | 0.64 mE | P | P | P |
| 15 | G | 1.00 Ex | G | 1.00 Ex | G | T S | G |
| 16 | R | 0.73 mE | G | 1.00 Ex | S A | E Q | G |
| 17 | S | 0.66 mE | S | 0.75 mE | S | T | S |
| 18 | L | 0.28 mB | L | 0.26 mB | V | L | L |
| 19 | R | 0.66 mE | K | 0.75 mE | R K | T S | R K |
| 20 | L | 0.00 Bu | C | 0.00 Bu | V | L | L |
| 21 | S | 0.71 mE | S | 0.82 Ex | S | T | S |
| 22 | C | 0.00 Bu | C | 0.00 Bu | C | C | C |
| 23 | S | 1.00 Ex | A | 1.00 Ex | K | T | A |
| 24 | S | 0.00 Bu | A | 0.00 Bu | A T V | F V | A |
| 25 | S | 0.87 Ex | S | 1.00 Ex | S | S | S |
| 26 | G | 1.00 Ex | G | 1.00 Ex | G | G | G |
| 27 | F | 0.10 Bu | F | 0.10 Bu | G Y D | F L G | F |
| 28 | I | 0.85 Ex | D | 0.72 mE | T | S | T N |
| 29 | F | 0.00 Bu | F | 0.00 Bu | F | L I | F |
| 30 | S | 0.74 mE | S | 0.83 Ex | S N V I | S | S |
| 36 | W | 0.00 Bu | W | 0.00 Bu | W | W | W |
| 37 | V | 0.00 Bu | V | 0.00 Bu | V | I | V |
| 38 | R | 0.10 Bu | R | 0.31 mB | R | R | R |
| 39 | Q | 0.15 Bu | Q | 0.28 mB | Q | Q | Q |
| 40 | A | 0.95 Ex | A | 0.75 mE | A | P | A |
| 41 | P | 0.90 Ex | P | 0.73 mE | P | P | P S |
| 42 | G | 1.00 Ex | G | 1.00 Ex | G | G | G |
| 43 | K | 0.86 Ex | K | 0.86 Ex | Q R K H | K R | K |
| 44 | G | 1.00 Ex | G | 1.00 Ex | G | A G | G S |
| 45 | L | 0.00 Bu | L | 0.00 Bu | L | L | L |

FIG. 1a

| Position | Fractional Accessibility KOL Residue Exposure | | J539 Residue Exposure | | Residues In Subgroup I | II | III |
|---|---|---|---|---|---|---|---|
| 46 | E | 0.75 mE | E | 0.73 mE | E | E | E |
| 47 | W | 0.10 Bu | W | 0.04 Bu | W | W | W |
| 48 | V | 0.00 Bu | I | 0.00 Bu | M V | L I | V |
| 49 | A | 0.00 Bu | G | 0.00 Bu | G | A G | G S A |
| 66 | R | 0.36 mB | K | 0.51 pB | R | R | R |
| 67 | F | 0.00 Bu | F | 0.00 Bu | V | L V | F |
| 68 | T | 0.87 Ex | I | 0.88 Ex | T | T | T |
| 69 | I | 0.00 Bu | I | 0.00 Bu | V M I | I V | I |
| 70 | S | 0.78 mE | S | 0.79 mE | T S | S T | S |
| 71 | R | 0.11 Bu | R | 0.00 Bu | R L A | K V | R |
| 72 | N | 0.61 mE | D | 0.55 pB | D K | D | D N |
| 73 | D | 0.44 pB | N | 0.43 pB | P E T A S | T | D N |
| 74 | S | 0.85 Ex | A | 0.97 Ex | S | S | S |
| 75 | K | 0.88 Ex | K | 0.77 mE | T F | K R | K |
| 76 | N | 0.69 mE | N | 0.68 mE | N S T | N | N |
| 77 | T | 0.41 pB | S | 0.33 mB | T Q | Q | T |
| 78 | L | 0.00 Bu | L | 0.00 Bu | A V | V F | L A |
| 79 | F | 0.45 pB | Y | 0.35 mB | Y | V S | Y F |
| 80 | L | 0.00 Bu | L | 0.00 Bu | M | L | L |
| 81 | Q | 0.53 pB | Q | 0.69 mE | E | T K S I N | Q |
| 82 | M | 0.00 Bu | M | 0.00 Bu | L | M L | M |
| 82a | D | 0.73 mE | S | 0.58 pB | S V R T | T S N I R | N D |
| 82b | S | 0.98 Ex | K | 0.96 Ex | S | N S | S |
| 82c | L | 0.00 Bu | V | 0.00 Bu | L | V M | L |
| 83 | R | 0.73 mE | R | 0.83 Ex | R F I | D T | R E |
| 84 | P | 0.75 mE | S | 0.90 Ex | S | P A | P A |
| 85 | E | 0.82 Ex | E | 0.90 Ex | E | V A | E D |
| 86 | D | 0.00 Bu | D | 0.11 Bu | D | D | D |
| 87 | T | 0.54 pB | T | 0.47 pB | T | T | T |
| 88 | G | 1.00 Ex | A | 0.00 Bu | A | A | A |
| 89 | V | 0.58 PB | L | 0.63 mE | V | T V | V L |
| 90 | Y | 0.00 Bu | Y | 0.00 Bu | Y | Y | Y |
| 91 | F | 0.00 Bu | Y | 0.08 Bu | Y | Y | Y |
| 92 | C | 0.00 Bu | C | 0.00 Bu | C | C | C |
| 93 | A | 0.00 Bu | A | 0.00 Bu | A | A | A T |
| 94 | R | 0.17 Bu | R | 0.15 Bu | R | R H | R P |
| | | | | | JH1 JH2 | JH3 | JH4 JH5 JH6 |
| 103 | W | 0.09 Bu | W | 0.07 Bu | W  W | W | W  W  W |
| 104 | G | 0.00 Bu | G | 1.00 Ex | G  G | G | G  G  G |

FIG. 1b

|  |  | Fractional Accessibility |  |  | Residues In Subgroup |  |  |  |  |  |
|---|---|---|---|---|---|---|---|---|---|---|
| Position Residue | KOL Exposure | Residue | J539 Exposure | I | II | | | III | | |
| | | | | JH1 | JH2 | JH3 | JH4 | JH5 | JH6 | |
| 105 | Q | 0.93 Ex | Q | 0.99 Ex | Q | R | Q | Q | Q | Q |
| 106 | G | 0.00 Bu | G | 0.00 Bu | G | G | G | G | G | G |
| 107 | T | 0.22 mB | T | 0.26 mB | T | T | T | T | T | T |
| 108 | P | 0.99 Ex | L | 0.67 mE | L | L | M | L | L | T |
| 109 | V | 0.00 Bu | V | 0.00 Bu | V | V | V | V | V | V |
| 110 | T | 0.76 mE | T | 0.69 mE | T | T | T | T | T | T |
| 111 | V | 0.00 Bu | V | 0.00 Bu | V | V | V | V | V | V |
| 112 | S | 0.98 Ex | S | 0.74 mE | S | S | S | S | S | S |
| 113 | S | 0.94 Ex | A | 0.84 Ex | S | S | S | S | S | S |

FIG. 1c

| Position | Residue | Exposure | I | II | III | IV | V | VI |
|---|---|---|---|---|---|---|---|---|
| 1 | Q | 1.00 Ex | Q | Q | S F | - | Q | N D |
| 2 | S | 1.00 Ex | S | S | Y | S | S | F |
| 3 | V | 0.77 mE | V | A | E | E | A | M |
| 4 | L | 0.00 Bu | L | L | L | L | L | L |
| 5 | T | 0.92 Ex | T | T | T K | T | T | T |
| 6 | Q | 0.00 Bu | Q | Q | Q | Q | Q | Q |
| 7 | P | 0.62 mE | P | P | P | D | P | P |
| 8 | P | 1.00 Ex | P | A R P | P | P | P | H |
| 9 | S | 1.00 Ex | S | S | S | A | S | S |
| 10 | - | - | - | - | - | - | - | - |
| 11 | A | 0.34 mB | A V | V | V | V | A | V |
| 12 | S | 0.71 mE | S | S | S | S | S | S |
| 13 | G | 1.00 Ex | G A | G | V L | V | G | E |
| 14 | T | 0.73 mE | T A | S | S A | A | S | S |
| 15 | P | 0.75 mE | P | P | P A | L | P L | P |
| 16 | G | 1.00 Ex | G | G | G | G | G | G |
| 17 | Q | 0.69 mE | Q | Q | Q | Q | Q | K |
| 18 | R | 0.79 mE | R | S | T | T | S | T |
| 19 | V | 0.21 mB | V | I V | A | V | V | V |
| 20 | T | 0.62 ME | T | T | R M | R | T | T |
| 21 | I | 0.00 Bu | I | I | I | I | I | I F M |
| 22 | S | 0.92 Ex | S | S | T | T | S | S |
| 23 | C | 0.00 Bu | C | C | C | C | C | C |
| 35 | W | 0.00 Bu | W | W | W | W | W | W |
| 36 | Y | 0.00 Bu | Y | Y F | Y | Y | Y | Y |
| 37 | Q | 0.46 pB | Q | Q | Q | Q | Q | Q |
| 38 | Q | 0.00 Bu | Q H | Q | Q E | Q | Q | Q |
| 39 | L | 0.75 mE | L V | H | K R | K | H | R |
| 40 | P | 0.91 Ex | P | P | P S | P | P A | P |
| 41 | G | 1.00 EX | G | G | G | G | G | G |
| 42 | M | 0.74 mE | T | K | Q R | Q | R K | S R G |
| 43 | A | 0.62 mE | A | A | A | A | A | A |
| 44 | P | 0.00 Bu | P | P | P | P | P | P |
| 45 | K | 0.95 Ex | K | K | V | L | K | T |
| 46 | L | 0.23 mB | L | L | M L P | L | L V | T |
| 47 | L | 0.15 Bu | L | M I L | V | V | V I | V |
| 48 | I | 0.00 Bu | I | I | I V | I | I | I |
| 49 | Y | 0.39 mB | Y | Y F | Y | Y | F Y | Y |
| 57 | G | 1.00 Ex | G | G | G E | G | G | G |
| 58 | V | 0.14 Bu | V I | V I | I V | I | V | V |
| 59 | P | 0.70 mE | P | S P | P | P | P | P |
| 60 | D | 0.95 Ex | D | D N L | E Q A | D | D | D |
| 61 | R | 0.31 mB | R | R | R | R | R | R |

FIG. 2a

| Position | | | Residues In Subgroup | | | | | |
|---|---|---|---|---|---|---|---|---|
| | Residue | Exposure | I | II | III | IV | V | VI |
| 62 | F | 0.12 Bu | F | F | F | F | F | F |
| 63 | S | 0.85 Ex | S | S | S | S | S | S |
| 64 | G | 0.00 Bu | G A | G | G S | G | G | G |
| 65 | S | 1.00 Ex | S | S | S Y | S | S | S |
| 66 | K | 0.41 pB | K | K | T S N | S | K | I F* |
| 67 | S | 1.00 Ex | S | S | S | S | S | S |
| 68 | G | 1.00 Ex | G | G | G | G | D G | S |
| 69 | A | 0.71 mE | T | N | T N | H | N | N |
| 70 | S | 1.00 Ex | S | T | T K S | T | T | S |
| 71 | A | 0.00 Bu | A | A | A V | A | A | A |
| 72 | S | 1.00 Ex | S T | S | T I | S | S | S |
| 73 | L | 0.00 Bu | L | L | L | L | L | L |
| 74 | A | 0.74 mE | A | T | T | T | T | T |
| 75 | I | 0.00 Bu | I | I | I | I | V | I |
| 76 | G | 1.00 Ex | S T | S | S N | T | S | S |
| 77 | G | 1.00 Ex | G | G | G R | G | G | G |
| 78 | L | 0.00 Bu | L | L | V A | A | L | L |
| 79 | Q | 0.76 mE | Q R | Q | Q E | Q | R Q | K Q T |
| 80 | S | 1.00 Ex | S T | A | A V | A | A | T |
| 81 | E | 0.78 mE | E G | E | E G | E | E | E |
| 82 | D | 0.09 Bu | D | D | D | D | D | D |
| 83 | E | 0.64 mE | E | E | E | E | E | E |
| 84 | T | 0.34 mB | A | A | A | A | A | A |
| 85 | D | 0.30 mB | D | D | D | D | D | D |
| 86 | Y | 0.00 Bu | Y | Y | Y | Y | Y | Y |
| 87 | Y | 0.16 Bu | Y | Y | Y F | Y | Y | Y |
| 88 | C | 0.00 Bu | C | C | C | C | C | C |
| | | | JL-1 | JL-2 | JL-3 | JL-4 | JL-5 | |
| 98 | F | 0.04 Bu | F | F | F | F | F | |
| 99 | G | 0.00 Bu | G | G | G | G | G | |
| 100 | T | 0.59 pB | T | G | G | S | S | |
| 101 | G | 1.00 Ex | G | G | G | G | G | |
| 102 | T | 0.00 Bu | T | T | T | T | T | |
| 103 | K | 0.82 Ex | K | K | K | Q | Q | |
| 104 | V | 0.00 Bu | V | L | L | L | L | |
| 105 | T | 0.86 Ex | T | T | T | T | T | |
| 106 | V | 0.19 Bu | V | V | V | V | V | |
| 106a | L | 0.70 mE | L | L | L | L | L | |
| 107 | G | 1.00 Ex | G | G | G | S | G | |

* additional residues after position 66:
  66a D
  66b S R D

FIG. 2b

| Position | Residue | Exposure | Residues In Subgroup | | | |
|---|---|---|---|---|---|---|
| | | | I | II | III | IV |
| 1 | E | 0.99 Ex | D | D | E | D |
| 2 | I | 0.16 Bu | I | I | I | I |
| 3 | V | 0.87 Ex | Q | V | V | V |
| 4 | L | 0.00 Bu | M | M | L | M |
| 5 | T | 0.80 mE | T | T | T | T |
| 6 | Q | 0.00 Bu | Q | Q | Q | Q |
| 7 | S | 0.89 Ex | S | S | S | S |
| 8 | P | 0.67 mE | P | P | P | P |
| 9 | A | 1.00 Ex | S | L | G | D N |
| 10 | I | 0.94 Ex | S | S | T | S |
| 11 | T | 0.30 mB | L | L | L | L |
| 12 | A | 0.59 pB | S | P | S | A |
| 13 | A | 0.00 Bu | A | V | L | V |
| 14 | S | 0.78 mE | S | T | S | S |
| 15 | L | 0.79 mE | V | P | P | L |
| 16 | G | 1.00 Ex | G | G | G | G |
| 17 | Q | 0.64 mE | D | E | E | E |
| 18 | K | 0.74 mE | R | P | R | R |
| 19 | V | 0.22 mB | V | A | A | A |
| 20 | T | 0.65 mE | T | S | T | T |
| 21 | I | 0.00 Bu | I | I | L | I |
| 22 | T | 0.69 mE | T | S | S | N |
| 23 | C | 0.00 Bu | C | C | C | C |
| 35 | W | 0.00 Bu | W | W | W | W |
| 36 | Y | 0.00 Bu | Y | Y | Y | Y |
| 37 | Q | 0.14 Bu | Q | L | Q | Q |
| 38 | Q | 0.24 mB | Q | Q | Q | Q |
| 39 | K | 0.69 mE | K | K | K | K |
| 40 | S | 1.00 Ex | P | P | P | P |
| 41 | G | 1.00 Ex | G | G | G | G |
| 42 | T | 0.90 Ex | K | Q | Q | Q |
| 43 | S | 0.30 mB | A | S | A | P |
| 44 | P | 0.00 Bu | P | P | P | P |
| 45 | K | 0.90 Ex | K | Q E R | R | K |
| 46 | P | 0.43 pB | L | L | L | L |
| 47 | W | 0.16 Bu | L | L | L | L |
| 48 | I | 0.00 Bu | I | I | I | I |
| 49 | Y | 0.42 pB | Y | Y | Y | Y |
| 57 | G | 1.00 Ex | G | G | G | G |
| 58 | V | 0.13 Bu | V | V | I | V |
| 59 | P | 0.61 mE | P | P | P | P |
| 60 | A | 1.00 Ex | S | D | D | D |
| 61 | R | 0.36 mB | R | R | R | R |
| 62 | F | 0.00 Bu | F | F | F | F |
| 63 | S | 0.94 Ex | S | S | S | S |

FIG.3a

| Position | | | Residues In Subgroup | | | |
|---|---|---|---|---|---|---|
| | Residue | Exposure | I | II | III | IV |
| 64 | G | 0.00 Bu | G | G | G | G |
| 65 | S | 1.00 Ex | S | S | S | S |
| 66 | G | 1.00 Ex | G | G | G | G |
| 67 | S | 1.00 Ex | S | S | S | S |
| 68 | G | 1.00 Ex | G | G | G | G |
| 69 | T | 0.75 mE | T | T | T | T |
| 70 | S | 0.98 Ex | D E Q | D | D | D |
| 71 | Y | 0.09 Bu | F | F | F | F |
| 72 | S | 0.70 mE | T | T | T | T |
| 73 | L | 0.00 Bu | L | L | L | L |
| 74 | T | 0.43 pB | T | K | T | T |
| 75 | I | 0.00 Bu | I | I | I | I |
| 76 | N | 0.83 Ex | S | S | S | S |
| 77 | T | 0.83 Ex | S | R | R | S |
| 78 | M | 0.00 Bu | L | V | L | L |
| 79 | E | 0.63 mE | Q | E Q | E | Q |
| 80 | A | 0.96 Ex | P | A | P | A |
| 81 | E | 0.91 Ex | E D | E | E | E |
| 82 | D | 0.13 Bu | D | D | D | D |
| 83 | A | 0.55 pB | F I | V | F | V |
| 84 | A | 0.00 Bu | A | G | A | A |
| 85 | I | 0.58 pB | T | V | V | V |
| 86 | Y | 0.00 Bu | Y | Y | Y | Y |
| 87 | Y | 0.11 Bu | Y | Y | Y | Y |
| 88 | C | 0.00 Bu | C | C | C | C |

| Position | Residue | Exposure | JK-1 | JK-2 | JK-3 | JL-4 | JL-5 |
|---|---|---|---|---|---|---|---|
| 98 | F | 0.00 Bu | F | F | F | F | F |
| 99 | G | 1.00 Ex | G | G | G | G | G |
| 100 | A | 1.00 Ex | Q | Q | P | G | Q |
| 101 | G | 0.00 Bu | G | G | G | G | G |
| 102 | T | 0.00 Bu | T | T | T | T | T |
| 103 | K | 0.79 mE | K | K | K | K | R |
| 104 | L | 0.00 Bu | V | L | V | V | L |
| 105 | E | 0.89 Ex | E | E | D | E | E |
| 106 | L | 0.44 pB | I | I | I | I | I |
| 106a | - | - | - | - | - | - | - |
| 107 | K | 0.77 mE | K | K | K | K | K |

FIG. 3b

Mouse Light Chain Variable Region
    5' upstream primer - FR1 of variable region
        5'- TCT CGG ATC CGA (CT)AT (TC)GT G(AC)T (GC)AC CCA (GA) -3'
           BamHI                               (SEQ ID NO: 1)

3' downstream primer - kappa constant region
        5'- TCT CAA GCT TTG GTG GCA AGA T(GA)G ATA CAG TTG GTG CAG C -3'
           Hind III                             (SEQ ID NO: 2)

Mouse Heavy Chain Variable Region
    5' upstream primer - FR1 of variable region
       i) 5'- TTC TGG ATC C(CG)A GGT (GCT)CA (AG)CT G(AC)A G(GC)A GTC (TA)GG -3'
           BamHI                               (SEQ ID NO: 3)

ii) 5'- TTC TGG ATC C(CG)A GGT (GCT)AA GCT GGT G(GC)A GTC (TA)GG -3'
           BamHI                               (SEQ ID NO: 4)

3' downstream primer - IgG2a CH1 region
        5'- TCT CAA GCT TAC CGA TGG (GA)GC TGT TGT TTT GGC -3'   (SEQ ID NO: 5)
           Hind III SHORTEN VERSION OF THE IgG4 HEAVY CHAIN CONSTANT REGION 5'- ATT TGG ATC C TC TAG A CA TCG CGG ATA GAC AAG AAC -3'   (SEQ ID NO: 6)
        BamHI   Xbal
    5'- AAT AAT GCG GCC GC A TCG AT G AGC TCA AGT ATG TAG ACG GGG TAC G -3'
          Not I    Cla I    Sac I                (SEQ ID NO: 7)

TK PROMOTER FRAGMENT
    5'- TAT AGA ATT C GG TAC CCT TCA TCC CCG TGG CCC G -3'   (SEQ ID NO: 8)
        EcoRI   Kpn I
    5'- TGC GTG TTC GAA TTC GCC -3'   (SEQ ID NO: 9)
               EcoRI

Ig H ENHANCER
    5'- TTT TAG ATC T GT CGA CAG ATG GCC GAT CAG AAC CAG -3'   (SEQ ID NO: 10)
         Bgl II   Sal I
    5'- TTG GTC GAC GGT ACC AAT ACA TTT TAG AAG TCG AT -3'   (SEQ ID NO: 11)
         Sal I    Kpn I

HUMAN KAPPA CONSTANT REGION
    5'- TCT CGG ATC CTC TAG AAG AAT GGC TGC AAA GAG C -3'   (SEQ ID NO: 12)
    5'- TCT CGC TAG CGG ATC CTT GCA GAG GAT GAT AGG G -3'   (SEQ ID NO: 13)

FIG. 4

Oligodeoxynucleotides for PCR Amplification of the LEN Light Chain
Variable Region (SEQ ID NO: 14)
S1  5'- CAT TCG CTT ACC AGA TCT AAG CTT ACT AGT GAG ATC ACA GTT CTC TCT AC -3'

V9  5'- TGG CTC TGC AGC TGA TGG TG -3'   (SEQ ID NO: 15)

V10 5'- CAC CAT CAG CTG CAG AGC CA -3'   (SEQ ID NO: 16)
V11 5'- CTG TCT GGG ATC CCA GAT TC -3'   (SEQ ID NO: 17)

V12 5'- GAA TCT GGG ATC CCA GAC AG -3'   (SEQ ID NO: 18)
V13 5'- GTT GCA ACA TCT TCA GCC TCC ACG CTG CTG ATG -3'   (SEQ ID NO: 19)

V14 5'- GTG GAG GCT GAA GAT GTT GCA ACT TAT TAC TG -3'   (SEQ ID NO: 20)
J3  5'- GAA TGT GCC TAC TTT CTA GAG GAT CCA ACT GAG GAA GCA AAG -3'   (SEQ ID NO: 21)

A1  5'- CAT TCG CTT ACC AGA TCT -3'   (SEQ ID NO: 22)
A2  5'- GAA TGT GCC TAC TTT CTA G -3'   (SEQ ID NO: 23)

Oligodeoxynucleotides for PCR Amplification of the m1B4
Heavy Chain Variable Region

V1  5'- CCC TCC AGG CTT CAC TAA GTC TCC CCC -3'   (SEQ ID NO: 24)

V2  5'- TTA GTG AAG CCT GGA GGG TCC CTG AAA CTC -3'   (SEQ ID NO: 25)
V3  5'- GCC CCT TCC CAG GAG CTT GGC GAA CCC AAG ACA TG -3'   (SEQ ID NO: 26)

V4  5'- AAG CTC CTG GGA AGG GGC TGG AGT TGG TCG CAG CC -3'   (SEQ ID NO: 27)
V5  5'- TGT TCA TTT GTA GGT ACA GGG TGT TCT TGG AAT TGT CTC TGG AGA TGG TG -3'
(SEQ ID NO: 28)
V6  5'- TGT ACC TAC AAA TGA ACA GTC TGA GGG CTG AGG ACA CAG CCT TGT ATT -3'
V7  5'- CTG TGA GAA GGG TGC CTT GGC CCC AGT AG -3'   (SEQ ID NO: 29)
                                                    (SEQ ID NO: 30)
V8  5'- AAG GCA CCC TTC TCA CAG TCT CCT CAG GTG -3'   (SEQ ID NO: 31)
J2  5'- GAA TGT GCC TAC TTA AGC TTT CTA GAG GAT CCT ATA AAT CTC TGG CCA TG -3'
(SEQ ID NO: 32)

S1, A1, and A2, as above

FIG. 5

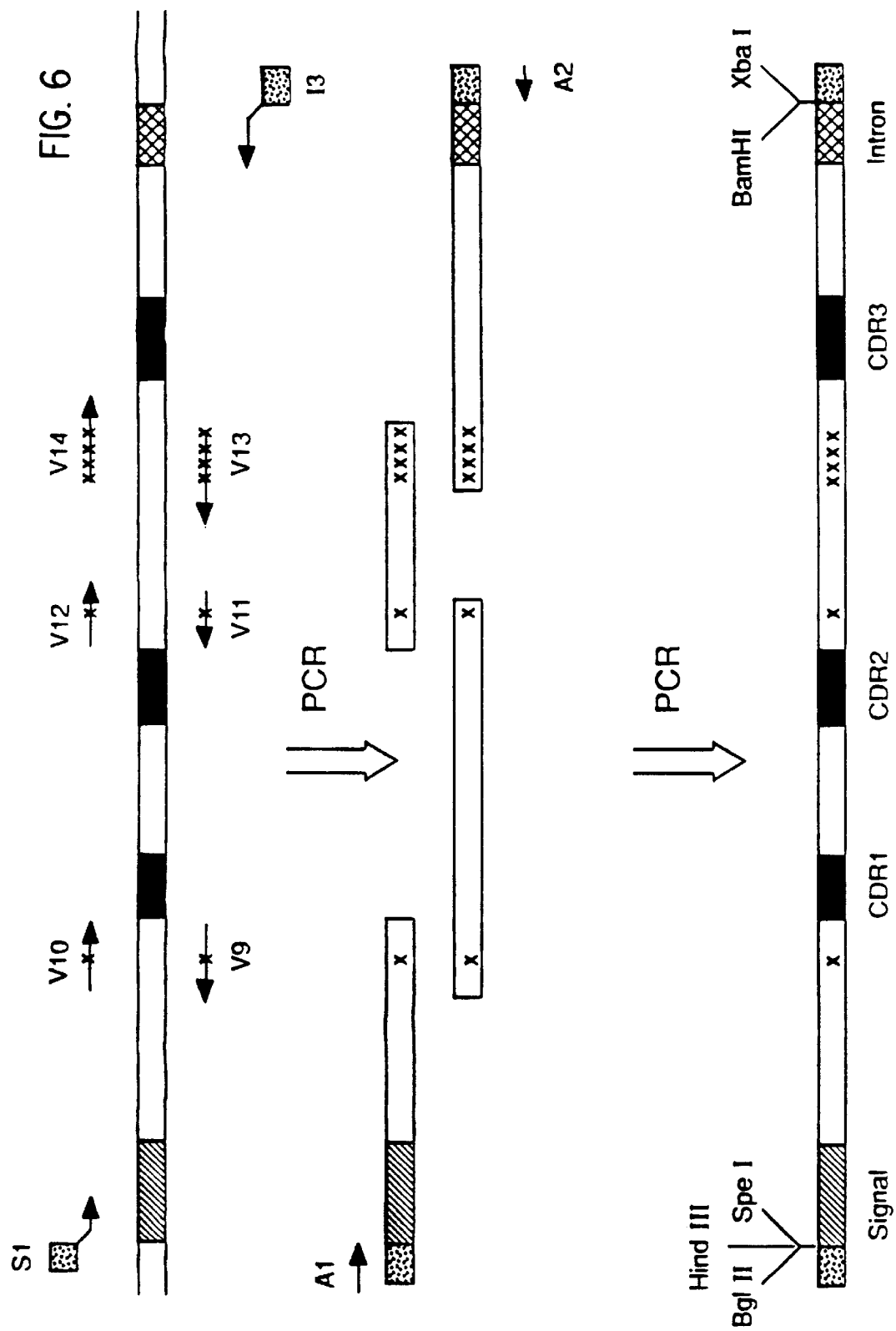

(CONT. ON FIG.7B)

HEAVY CHAIN

```
              √                                    √
v1B4: DVKLVESGGDLVKPGGSLKLSCAASGFTFS [DYYMS] WVRQAP
m1B4: DVKLVESGGDLVKLGGSLKLSCAASGFTFS [DYYMS] WVRQTP
 Gal: EVQLVESGGDLVQPGRSLRLSCAASGFTFS [BLGMT] WVRQAP

√ √                                  √
GKGLELVA [AIDNDGGSISYPDTVKG] RFTISRDNSKNTLYLQM
EKRLELVA [AIDNDGGSISYPDTVKG] RFTISRDNAKNTLYLQM
GKGLEWVA [NIKZBGSZZBYVDSVKG] RFTISRDNAKNSLYLQM

√  √                         √
NSLRAEDTALYYCAR [-QGRLRRDYFDY] WGQGTLLTVSS....
SSLRSEDTALYYCAR [-QGRLRRDYFDY] WGQGTTLTVSS...
NSLRVEDTALYYCAR [-----GWGGGD-] WGQGTLVTVST...
                               (SEQ ID NO: 33)
                               (SEQ ID NO: 34)
                               (SEQ ID NO: 35)
```

LIGHT CHAIN

```
            √          √       √
v1B4: DIVMTQSSNSLAVSLGERATISC [RASESVDSYGNSFMH--] WY
m1B4: DIVLTQSPASLAVSLGQRATISC [RASESVDSYGNSFMH--] WY
 Len: DIVMTQSSNSLAVSLGERATINC [KSSQSVLYSSNSKNYLA] WY

√         √        √√
QQKPGQPPKLLIY [RASNLES] GIPDRFSGSGSGTDFTLTISSV
QQKPGQPPKLLIY [RASNLES] GIPARFSGSGSRTDFTLTINPV
QQKPGQPPKLLIY [WASTRES] GVPDRFSGSGSGTDFTLTISSL

√                  √      √
EAEDVATYYC [QQSNEDPLT] FGQGTKLEIKR... (SEQ ID NO: 36)
EADDVATYYC [QQSNEDPLT] FGAGTKLELKR... (SEQ ID NO: 37)
QAEDVAVYYC [QQYYSTPYS] FGQGTKLEIKR... (SEQ ID NO: 38)
```

METHOD FOR REDUCING THE IMMUNOGENICITY OF ANTIBODY VARIABLE DOMAINS

RELATED APPLICATIONS

This application is a continuation of application Ser. No. 08/905,280, filed Aug. 1, 1997, now abandoned, which is a continuation of application Ser. No. 08/609,218, filed Mar. 1, 1996, now abandoned, which is a continuation of application Ser. No. 08/109,187, filed Aug. 19, 1993, now abandoned, which is a continuation-in-part of application Ser. No. 07/702,217, filed May 17, 1991, now abandoned.

BRIEF DESCRIPTION OF THE DRAWINGS

FIGS. 1A–1C. Solvent exposure of sidechains of framework residues in KOL and J539 Fvs and the residues which occur most frequently at these positions in the various human VH subgroups.

FIGS. 2A and 2B. Solvent exposure of sidechains of framework residues in KOL VL and the residues which occur most frequently at these positions in the various human V-lambda subgroups.

FIGS. 3A and 3B. Solvent exposure of sidechains of framework residues in J539 VL and the residues which occur most frequently at these positions in the various human V-kappa subgroups.

FIG. 4. Primers used to isolate DNA encoding murine kappa light chain variable region and murine IgG2a heavy chain variable region using PCR. Oligodeoxynucleotides used as PCR primers to generate a shortened IgG4 heavy chain. Oligodeoxynucleotides used in PCR to re-engineer the thymidine kinase (TK) promoter to facilitate the expression of the neomycin resistance gene. Oligodeoxynucleotide primers used in PCR to clone the IgH enhancer sequence. Oligodeoxynucleotides used as PCR primers to generate a human kappa light chain constant region.

FIG. 5. Oligodeoxynucleotides used in the construction of the "veneered" 1B4 heavy and light chain variable regions plus those necessary to fuse the human signal and intronic sequenceds onto these variable regions.

FIG. 6. PCR-recombination strategy used in the veneering of the 1B4 kappa light chain variable region.

FIGS. 11A–10C. Outline of the insertion of hygromycin selectable expression vector.

FIG. 12. Amino acid sequence compleition of the "veneered"-1B4, murine 1B4 and human Gal heavy chain variable regions and the "veneered" 1B4, murine 1B4 and human Len kappa light chain variable regions. Check marks idicate the individual amino acid residues converted.

BACKGROUND OF THE INVENTION

Figure 7A:
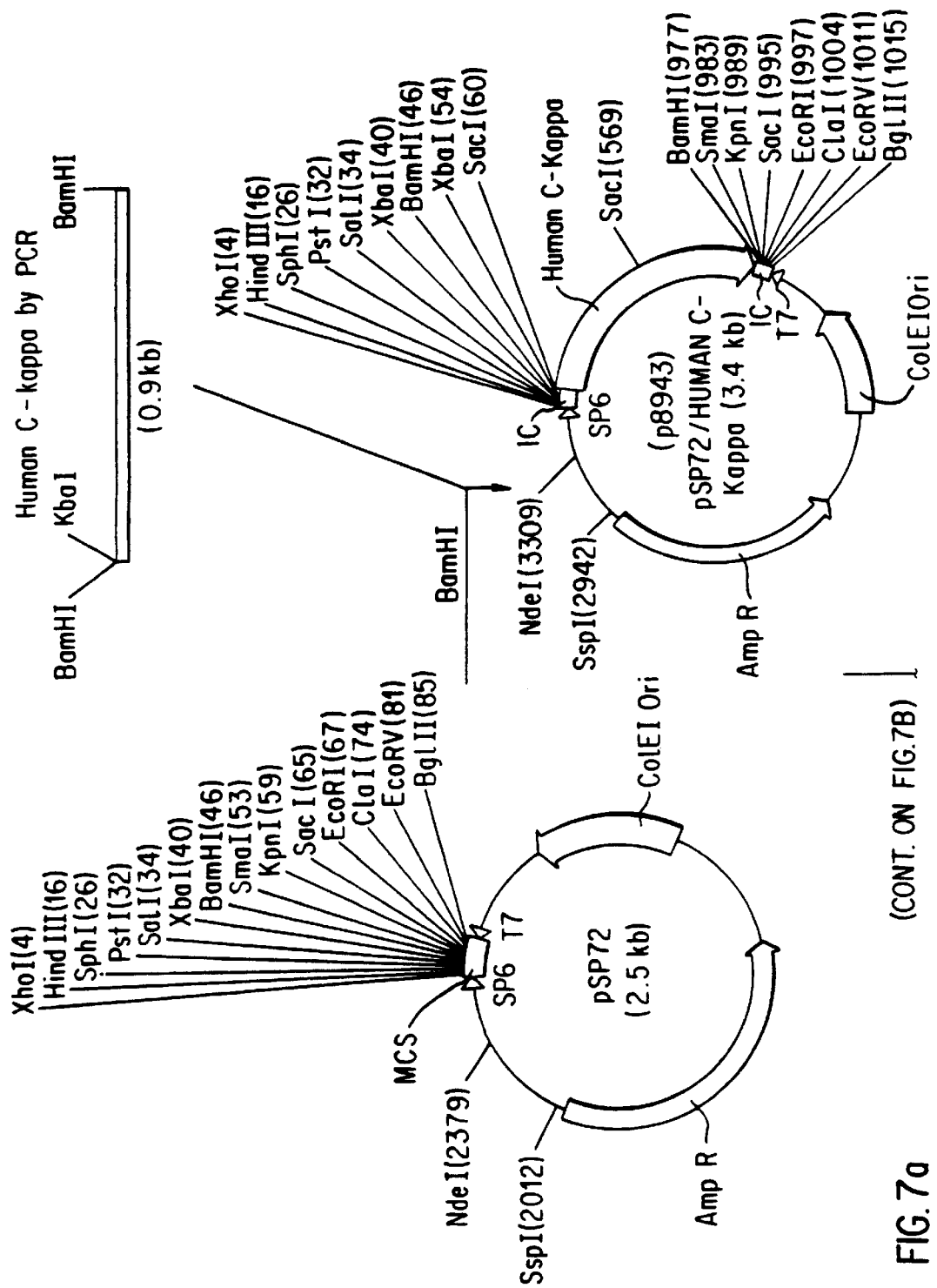
FIGS. 7A–7C. Outline of the insertion of the "veneered" kappa light chain variable region and kappa constant region into the light chain expression vector.

The identification and production of murine monoclonal antibodies has lead to numerous therapeutic applications of these exquisitely specific molecules in human disease. The technologies of molecular biology have further expanded the utility of many antibodies by allowing for the creation of class switched molecules whose functionality has been improved by the acquisition or loss of complement fixation. The size of the bioactive molecule may also be reduced so as to increase the tissue target availability of the antibody by either changing the class from an IgM to an IgG, removing most of the heavy chain constant region in the creation of a F(ab)2 or both heavy and light chain constant regions maybe dispensed with in the formation of a Fv antibody. Common to all of these potentially therapeutic forms of antibody are the requisite CDRs (complementary determining regions) which guide the molecule to its ligand and the framework residues (FRs) which support these latter structures and dictate the disposition of the CDRs relative to one another, Winter European Patent Application, Publication No. 239, 400; Riechmann et al., Nature 332: 323–327 (1988). Crystallographic analyses of numerous antibody structures reveal that the combining site is composed almost entirely of the CDR residues arranged in a limited number of loop motifs, Padlan and Sheriff, 1990. The necessity of the CDRs to form these structures combined with the appreciated hypervariablity of their primary sequence leads to a great diversity in the antigen combining site, but one which has a finite number of possibilities. Thus, hypermutability and a limited primary sequence repetoire for each CDR would suggest that the CDRs derived for a given antigen from one species of animal would be the same derived from another species. Hence, they should be poorly immunogenic, if at all, when presented to a recipient organism in a non-foreign context.

Monoclonal antibody producing hybridomas have been most readily obtained from immunized rodents. Development of similar reagents from human sources has been frustrated by the current inability to maintain long term cultures of cells which produce sufficient quantities of antibody. Additional problems arise from the regulatory standpoint when cells of human origin are employed for the production of agents to be used in man. These considerations have led to the widespread use of rodent mono-clonal antibodies for the imaging and treatment of malignancy, prophyllactic administration to guard against toxic shock, modification of graft rejection episodes, and to temper acute inflammatory reactions. In all scenarios where completely rodent or partially rodent (ie, rodent—human chimeras) antibodies have been used for therapy the recipients have often illicited an immune response directed toward the antibody. These reactions have limited the duration and effectiveness of the therapy.

Various attempts have been made to minimize or eliminate the immunogenicity of non-human antibodies while preserving their antigen-binding properties. Initially, chimeric antibodies were constructed containing the rodent variable regions and their associated CDRs fused to human constant domains. The following references generally describe chimeric antibody technology: Lobuglio et al., Proc. Natl. Acad. Sci. USA 86: 4220–4224 (1989); U.S. Pat. No. 4,816,567; PCT International Publication No. WO 87/02671, published May 7, 1987; European Patent Publication No. 255,694, published Feb. 10, 1988; European Patent Publication No. 274,394, published Jul. 13, 1988; European Patent Publication No. 323,806, published Jul. 12, 1989; PCT International Publication No. WO/89/00999, published Feb. 9, 1989; European Patent Publication No. 327,000, published Aug. 9, 1989; European Patent Publication No. 328,404, published Aug. 16, 1989; and European Patent Publication No. 332,424, published Sep. 13, 1989. These proved to be less immunogenic but still approximately half of the recipients mounted an immune response to the rodent variable region framework residues. Further reduction of the "foreign" nature of the chimeric antibodies has been achieved by grafting only the CDRs from the rodent monoclonal into a human supporting framework prior to its subsequent fusion with an appropriate constant domain, Winter European Patent Application, Publication No. 239,400; Riechmann et al., *Nature* 332: 323–327 (1988). The procedures employed to accomplish CDR-grafting often result in imperfectly "humanized" antibodies. That is to say, the resultant antibody has either lost avidity (usually 2–3 fold, at best) or in an attempt to retain its original avidity a significant number of the murine framework residues have replaced the corresponding ones of the chosen human fromework. In this later case, the immunogenicity of the modified "humanized" antibody is difficult to anticipate a priori.

The ligand binding characteristics of an antibody combining site are determined primarily by the structure and relative disposition of the CDRs, although some neighboring residues also have been found to be involved in antigen binding (Davies et al., *Ann. Rev. Biochem.* 59: 439–473 [1990]). Fine specificity can be perserved in a "humanized" antibody only if the CDR structures, their interaction with each other, and their interaction with the rest of the variable domains are strictly maintained. One may anticipate that the key residues represent "interior" and interdomain contact residues, hence those surface exposed residues which are immediately available for immune surveillance should be non-inclusive of the structural residues.

OBJECTS OF THE INVENTION

It is, accordingly, an objective of the present invention to provide a means of converting a monoclonal antibody of one mammalian species to a monoclonal antibody of another mammalian species. Another object is to identify the amino acid residues responsible for species specificity or immunogenicity on the exterior of the monoclonal antibody. Another object is judiciously replace or veneer the exterior amino acid residues of one species with those of a second species so that the antibodies of the first species will not be immunogenic in the second species. A further object is to make replacements only in framework regions of the heavy and light chains of the antibody molecule and not in the complementarity-determining regions. Another object of the invention is to provide novel DNA sequences incorporating the replacement amino acid residues. Another object is to provide a vector containing the DNA sequences for the altered antibody. Another object is to provide a eukaryotic or procaryotic host transformed with a vector containing the DNA sequence for the veneered antibody.

SUMMARY OF THE INVENTION

A unique method is disclosed for identifying and replacing immunoglobulin surface amino acid residues which converts the antigenicity of a first mammalian species to that of a second mammalian species. The method will simultaneously change immunogenicity and strictly preserve ligind binding properties. The judicious replacement of exterior amino acid residues has no effect on the ligand binding properties but greatly alters immunogenicity.

DETAILED DESCRIPTION OF THE INVENTION

The present invention relates to a "humanization" procedure which simultaneously reduces the immunogenicity of the rodent monoclonal antibody while preserving its ligand binding properties in their entirety. Since the antigenicity of a protein is primarily dependent on the nature of its surface, the immunogenicity of an xenogenic or allogenic antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is refered to as "veneering" since only the outer surface or skin of the antibody is altered, the supporting residues remain undisturbed.

The procedure for "veneering" makes use of the available sequence data for human antibody variable domains compiled by Kabat et al., "Sequences of Proteins of Immunological Interest", 4th ed., Bethesda, Md.: National Institutes of Health, 1987, updates to this database, and other accessible U.S. and foreign databases (both nucleic acid and protein). The subgroups into which the various sequences have been combined are presented in FIGS. 1–3, indicating the most frequently occurring amino acid at each framework position. Also presented are the sequences of the various J-minigenes. The solvent accessibilities of the amino acids, as deduced from the known three-dimensional structure for human and mouse antibody fragments, are included in these figures.

High resolution X-ray crystallography of the variable domains of the antibodies KOL and J539 have been subjected to extensive refinement beginning with the structures available from the Protein Data Bank (Bernstein et al., *J. Mol. Biol.* 112: 535–542 1977; file 2FB4 for KOL and file 2FBJ for J529). The solvent accessibilities were computed as described by Padlan Proteins: Struct. Funct. Genet. 7: (1990).

There are two steps in the process of "veneering". First, the framework of a first animal species, i.e. the mouse, variable domains are compared with those corresponding frameworks of a second animal species, i.e. human. It is intended that this invention will allow the antigenic alteration of any animal species antibody. The present invention is illustrates the conversion of murine antibody to human antibody, but this is for illustrative purposes only. The most homologous human variable regions are then compared residue for residue to the corresponding murine regions. This will also define the human subgroup to which each mouse sequence most closely resembles. Second, those residues in the mouse framework which differ from its human counterpart are replaced by the residues present in the human counterpart. This switching occurrs only with those residues which are at least partially exposed (mE and Ex; FIGS. 1–3). One retains in the "veneered" mouse antibody: its CDRs, the residues neighboring the CDRs, those residues defined as buried or mostly buried (mB and Bu; FIGS. 1–3), and those residues believed to be involved with interdomain contacts (boldface, FIGS. 1–3).

Human and murine sequences frequently differ at the N-terminus of both heavy and light chains. The N-termini are contiguous with the CDR surface and are in position to be involved in ligand binding. Thus, wisdom would dictate that these murine termini be retained in its "veneered" version.

Finally, replacement of some amino acid types could have a significant effect on the tertiary structure or electrostatic interactions of the variable region domains. Hence, care should be exercised in the replacement of proline, glycine, and charged amno acids.

These criteria and the following procedures are used to prepare recombinant DNA sequences which incorporate the CDRs of a first mammalian species, animal, mMAb, both light and heavy chains, into a second mammalian species, human, appearing frameworks that can be used to transfect mammalian cells for the expression of recombinant human antibody with the antigen specificity of the animal monoclonal antibody. The present invention further comprises a method for constructing and expressing the altered antibody comprising: (i) mutagenesis and assembly of variable region domains including CDRs and mutagenesis and assembly of variable region domains including CDRs and FRs regions; (ii) preparation of an expression vector including at least one variable region which upon transfection into cells results in the secretion of protein sufficient for avidity and specificity determinations; and (iii) co-amplification of heavy and light chain expression vectors in appropriate cell lines. The present invention provides recombinant methods for incorporating CDRs from animal monoclonal antibodies into frameworks which appear to be human immunoglobulin in nature so that the resulting recombinant antibody will be either weakly immunogenic or non-immunogenic when administered to humans. Preferably the recombinant immunoglobulins will be recognized as self proteins when administered for threapeutic purposes. This method of "veneering" will render the recombinant antibodies useful as therapeutic agents because they will be either weakly immunogenic or non-immunogenic when administered to humans. The invention is further contemplated to include the recombinant conversion of any animal monoclonal antibody into a recombinant "human-appearing" monoclonal antibody providing that a suitable framework region can be identified (as described below). The animal monoclonals may include, but are not limited to, those murine monoclonal antibodies described by VanVoorhis et al., *J. Exp. Med.* 158: 126–145 (1983) which bind to human leukocytes and the appropriate mMAbs produced by hybridomas deposited in the Hybridoma Cell Bank maintained by the American Type Culture Collection (ATCC) and described in the ATCC Catalog of Cell Lines 8 Hybridomas, No. 6, 1988.

The CDR sequences from the animal monoclonal antibody are derived as follows. Total RNA is extracted from the murine hybridomas, for example the 1B4 myeloma cells described by Wright et al., *Proc. Natl. Acad. Sci. USA* 80: 5699–5703 (1983), the 60.3 cells described by Beatty et al., J. Immunol. 131:2913–2918 (1983), the TS1/18 cells described by Sanchez-Madrid et al., *J. Exp. Med.* 158: 1785–1803 (1983), and other anti-CD18 or CD11 monoclonal antibodies and hybridomas as described in Leukocyte Typing 111, Springer-Verlag, New York (1988), using standard methods involving cellular solubilization with guanidinium isothiocyanate (Chirgwin et al., *Biochem.* 18: 5294–5299 [1979]). The murine 1B4 mMAb will be used as the primary example of animal MAb that can be "veneered" by the unique process being disclosed. The invention is intended to include the conversion of any animal immunoglobulin to a "human-appearing" immunoglobulin. It is further intended that "human-appearing" immunoglobulin (Ig) can contain either kappa or lambda light chains or be one of any of the following heavy chain isotypes (alpha, delta, epislon, gamma and mu).

Pairs of degenerate oligodeoxynucleotide primers (FIG. 4) representing sequences within framework 1 of the murine kappa light chain variable region and light chain constant domain, or those within framework 1 of the murine IgG2a heavy chain variable region and heavy chain constant CH1 domain are synthesized on an Applied Biosystem 381A DNA synthesizer, removed from the resin by treatment with concentrated NH40H and desalted on a NAP-5 column eluted with $H_2O$. Total RNA, about 2 $\mu$g, is reverse transcribed for 30 min at 42° C. using Moloney MLV reverse transcriptase, about 200 units (BRL), and about 10 pmoles of the constant region complementary strand primers for either the heavy or light chain. The reverse transcriptase is heat inactivated, about 95° C. for about 5 min, and the reactions are made to contain in about 100 $\mu$l of PCR buffer about 50 pmoles of each of the paired primers and and 2.5 units of Taq polymerase. About 45 cycles of amplification (2', 94° C.; 2', 55° C.; 2' 72° C.) are followed by gel purification of the anticipated 400+base pair (bp) DNA fragments. Prior to subcloning those DNAs into a blunt-ended intermediate plasmid such as pSP72 (Promega) they are terminally phosphorylated using T4 polynucleotide kinase. Multiple clones representing these PCR amplified sequences are grown and submitted to DNA sequence determinations using Sequenase® and T7 and SP6 specific sequencing primers. A unique DNA sequence representing a murine IgG2a heavy chain variable region is obtained by analysis of the derived amino acid sequences. Replacement of the "murine-appearing" framework residues with those residues compatible with a human variable region is accomplished utilizing the following unique processes. An appropriate human framework is determined utilizing the criteria discussed below. The light chain variable region framework with sufficient homology to the the m1B4 framework was determined to be the human LEN framework (FR). The Len FR shows a similarity of 90% and an identity of 81% when compared to murine 1B4. This sequence, with its leader, 3' intronic sequences and engrafted m1B4 CDRs had been subcloned into the intermediate vector pGEM3Z (Promega), as described in Daugherty et al. *Nucleic Acids Res.* 19: (1991). About eight oligodeoxynucleotide primers (FIG. 5) are synthesized representing the primers necessary to generate by polymerase chain reaction (PCR) amplification four DNA fragments. Incorporated into all but the terminal oligodeoxynucleotide primers were those sequences corresponding to the veneered MAb 1B4 light chain, with its unaltered CDRs, and at least 15 bases of 5'-terminal complementarity to allow for the subsequent PCR-directed recombination of these four fragments. For the purposes of exemplifying the "veneering" process the LEN light chain variable region already containing an engrafted set of CDRs representing those within the light chain of murine 1B4 was used as the template into which mutations were placed so as to easily create the "veneered" framework sequence. The appropriate primer pair (S1 & V9, V10 & V11, etc.), about 50 pmole each, was combined with about 10 ng of plasmid DNA representing the LEN CDR-grafted framework, about 2.5 units of Taq DNA polymerase and about twenty-five (25) cycles of PCR amplification ensued (cycle periods: 1', 94° C.; 1', 55° C.; 2' 72° C.). The products of the four reactions, purified by agarose gel electrophoresis, are combined, about 10 ng of each DNA fragment, along with terminal oligodeoxynucleotide primers (A1 & A2, FIG. 6) and Taq DNA polymerase. The combined fragments were PCR amplified (25 cycles of: 2', 94° C.; 2', 55° C.; 2' 72° C.). Following restriction endonuclease digestion with Hind 111 and Xba I the amplified DNA is purified by agarose gel electrophoresis and subcloned into compatible sites of an intermediate vector pSP72 (Promega) which contains the human kappa light chain constant region (see FIG. 7). Genomic DNA, about 1 μg, purified from a human B cell line (GM0108A: NIGMS Human Genetic Mutant Cell Repository, Institute for Medical Research, Camden, N.J.) is used as a template for PCR amplification (FIG. 4) of about a 920 base pair fragment containing the splice acceptor for the kappa light chain constant domain, the exon and a portion of its 3'-untranslated region. The PCR product is purified by agarose gel electrophoresis, digested with Bam H1 endonuclease, and subcloned into pSP72 previously linearized with Bam H1. The individual clones representing the pSP72 intermediate vector containing both the 1B4 "veneered" light chain variable region and the human kappa constant region derived by PCR amplification of human DNA are used to determine the DNA sequence of the "veneered" light chain variable region.

Figure 8:
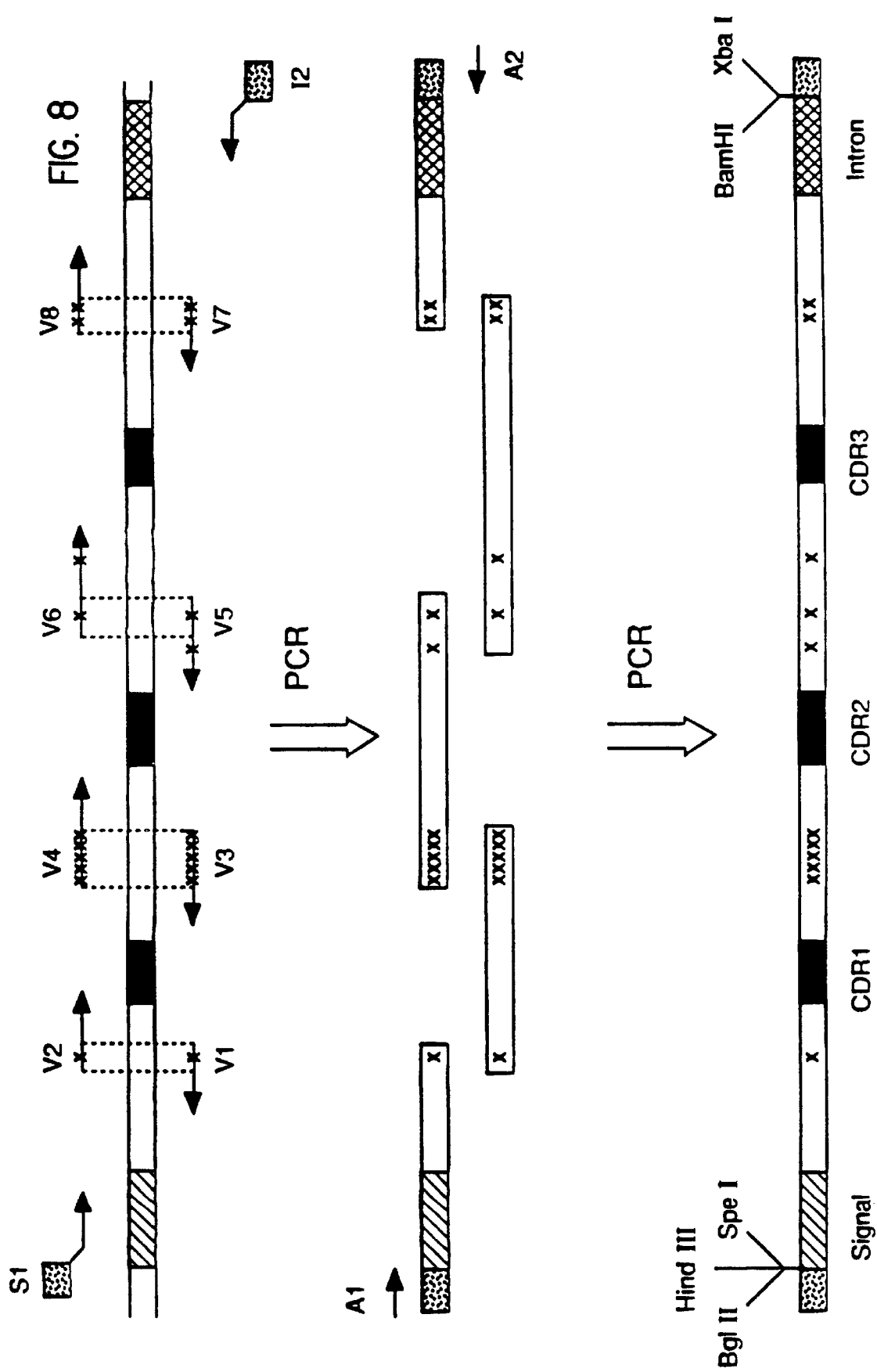
FIG. 8. PCR-recombination strategy used in the veneering of the 1B4 heavy chain variable region.

The "veneered" heavy chain portion of the recombinant antibody is derived from the mutated version of the murine 1B4 heavy chain variable region fused to the human constant region of a gamma 4 subtype obtained from a lambda library constructed by Flanagan and Rabbits, Nature 300: 709–713 (1982). The variable region of the "veneered" heavy chain is constructed from five DNA fragments representing a signal sequence, portions of the mutated murine heavy chain variable region, and an intronic sequence (FIG. 8). Oligodeoxynucleotide primer pairs (FIG. 5) are synthesized representing the primers necessary to generate by PCR amplification these five DNA fragments from about 10 ng of plasmid DNA template obtained from a pSP72 intermediate vector containing the heavy chain variable region previously used to determine the murine 1B4 CDR sequence. Amplification of the signal fragment, variable region fragments, and intron-containing fragment was as described above. The agarose gel purified products are combined, about 10 ng of each product, with terminal oligodeoxynucleotide primer pairs (FIG. 8) and the PCR-generated in vitro recombined template is amplified using the standard procedures described above. Prior to subcloning into a Hind 111 and Bam H1 digested expression vector containing the human heavy chain gamma 4 constant region (FIG. 9), this recombined product is similarly digested and agarose gel purified. Individual clones are submitted to DNA sequence determination using Sequenase® and T7 and SP6 specific sequencing primers and one is chosen for subsequent expression. The gamma 4 heavy chain constant region is subcloned as about a 6.7 Kb Hind 111 fragment derived from the plasmid pAT84 into the Hind 111 site of the intermediate vector pSP72. This plasmid is then used as the template DNA from which a shortened version of the gamma 4 constant region is subcloned using PCR amplification and the primer pairs indicated in FIG. 4. Eukaryotic expression vectors are constructed as described below.

Figure 10A:
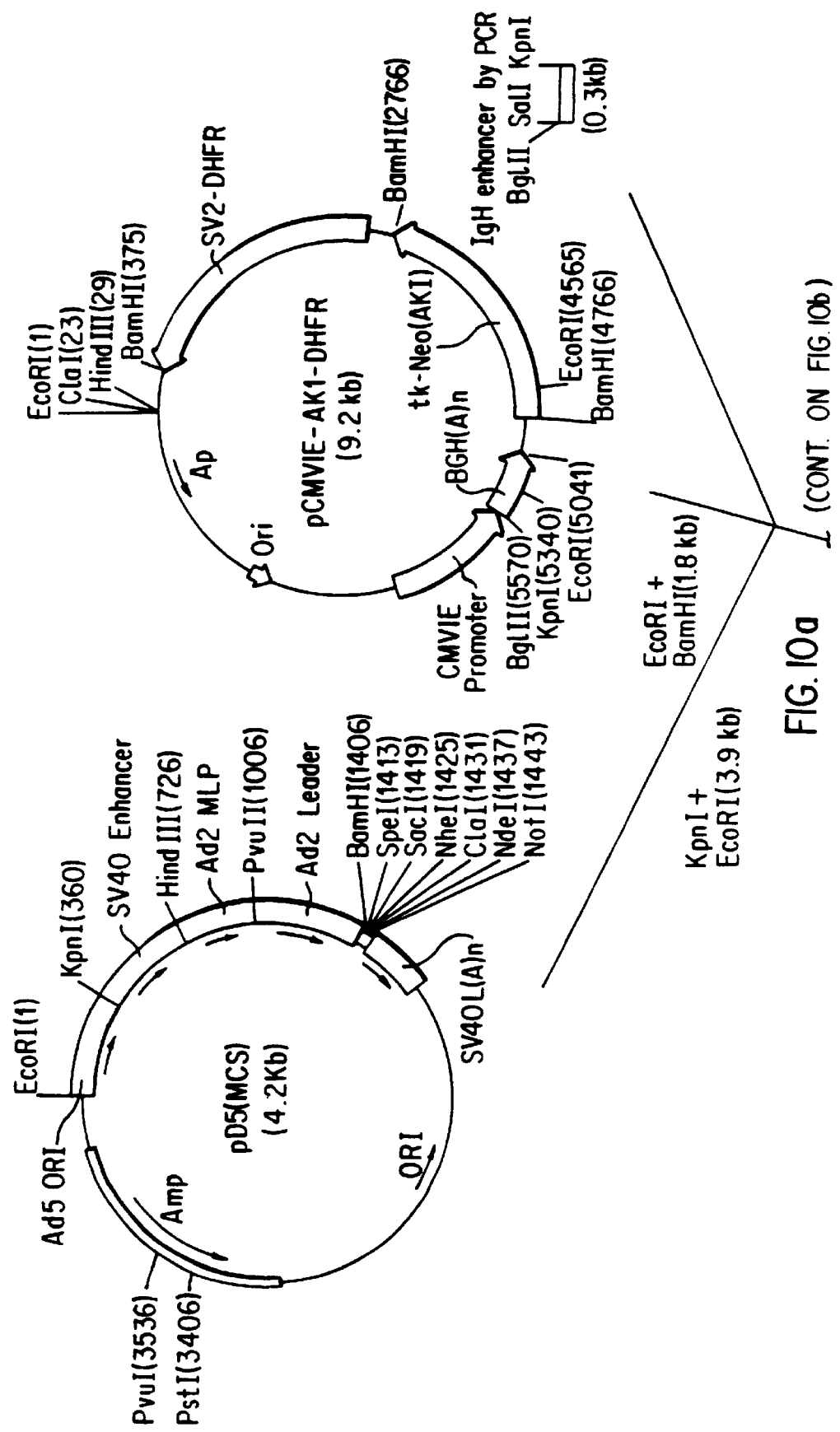
FIGS. 10A and 10B. Outline of the insertion of neomycin selectable expression vector.
Figure 10B:
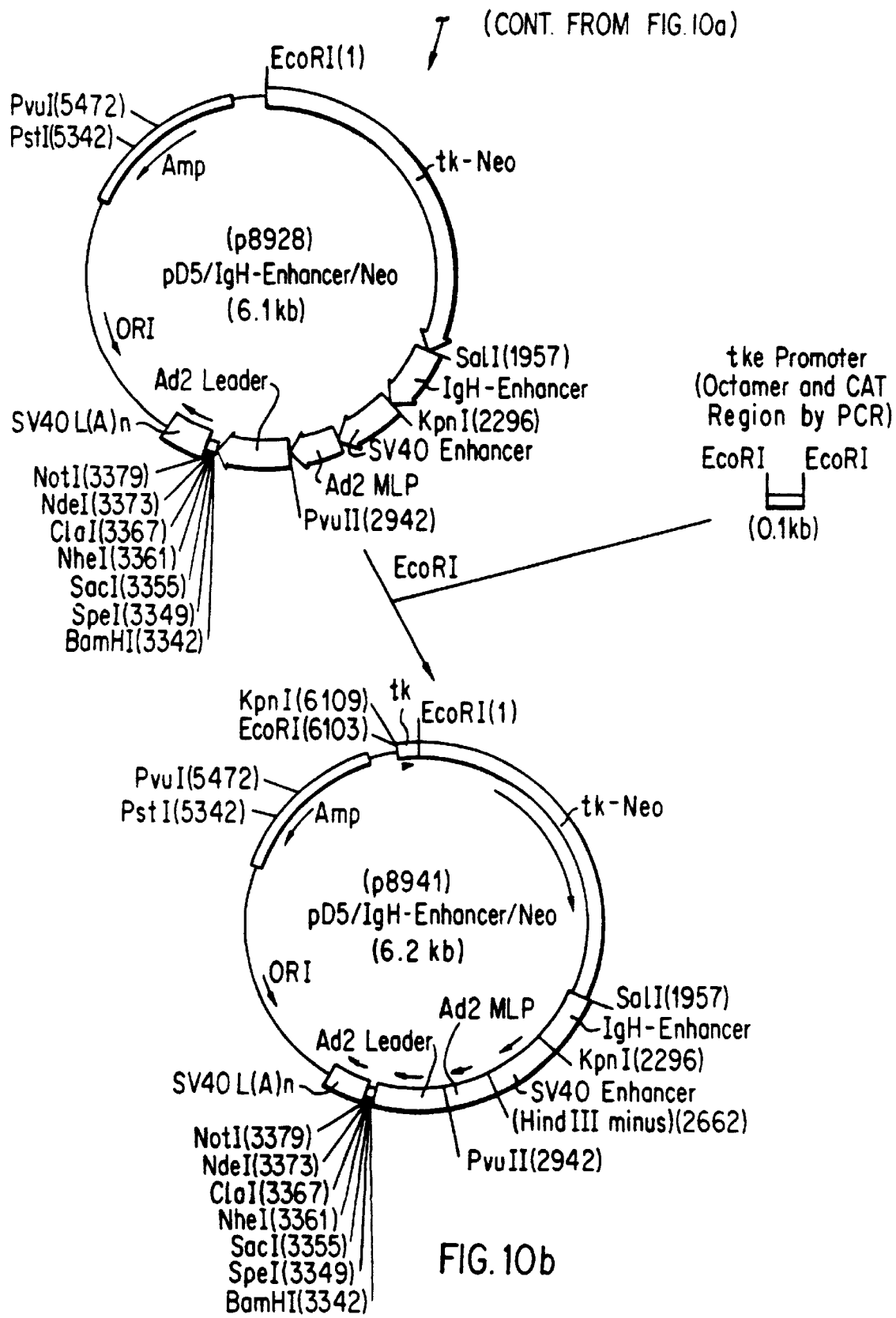
Figure 11A:
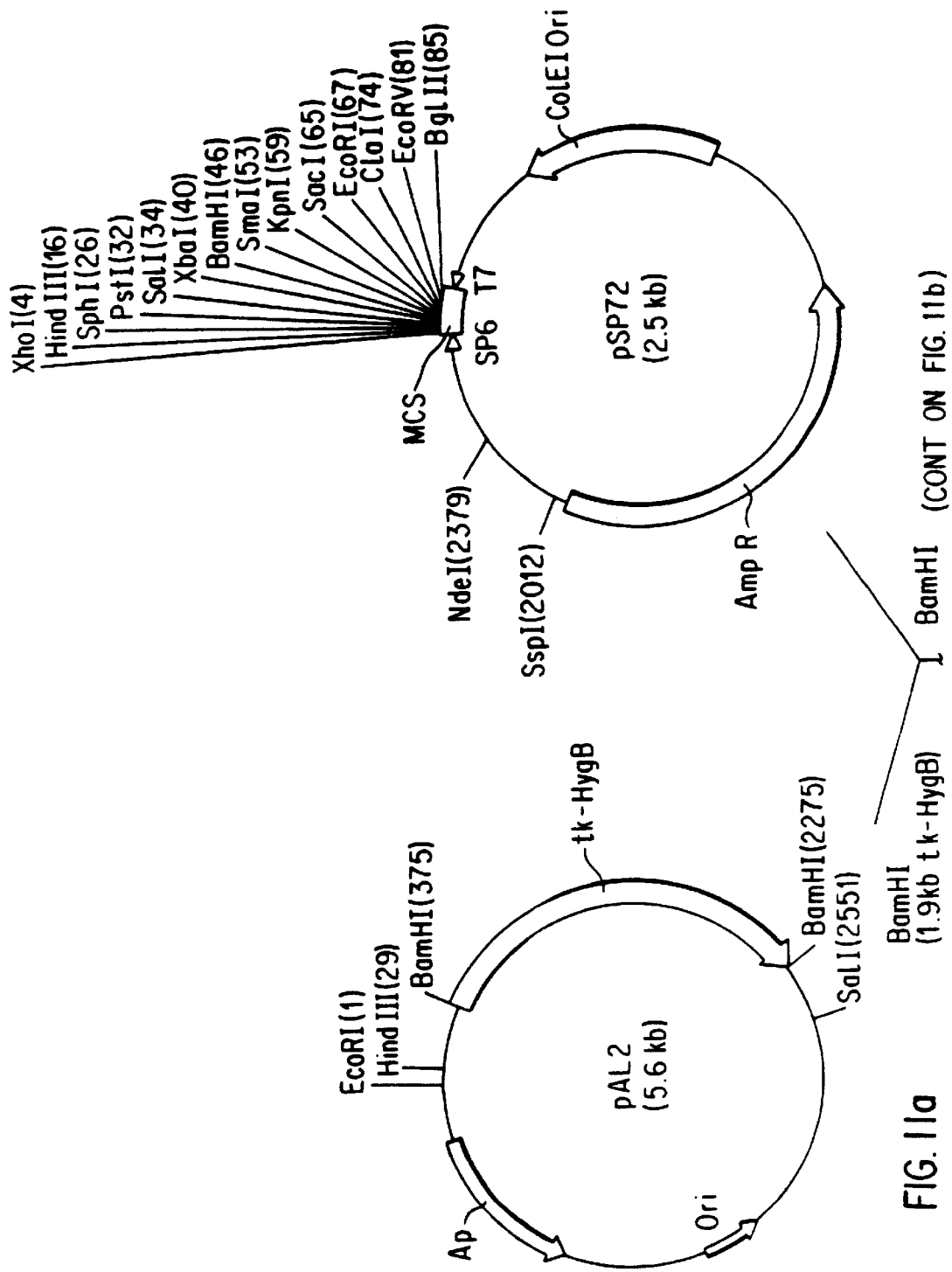
Figure 11B:
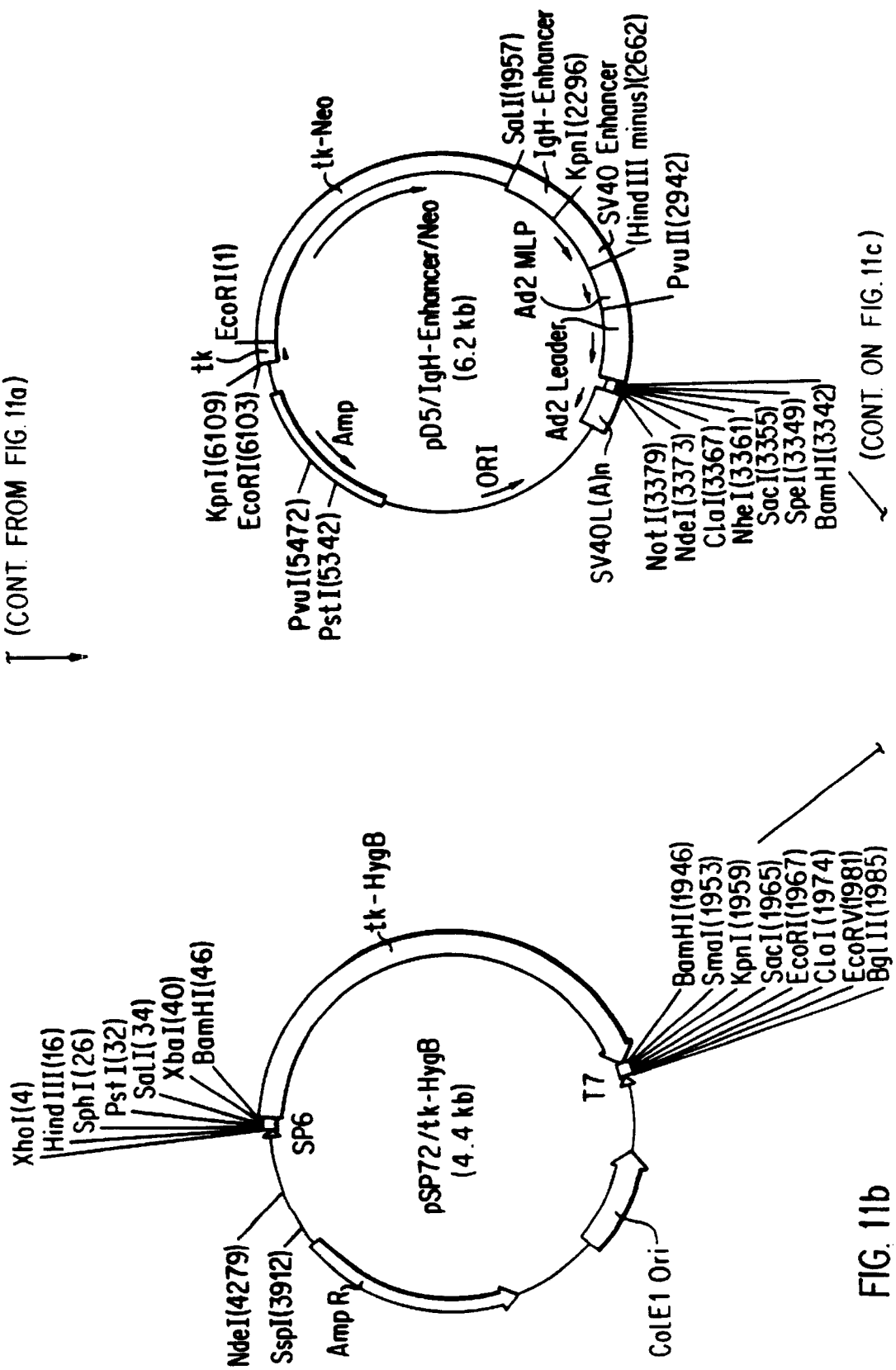
Figure 11C:
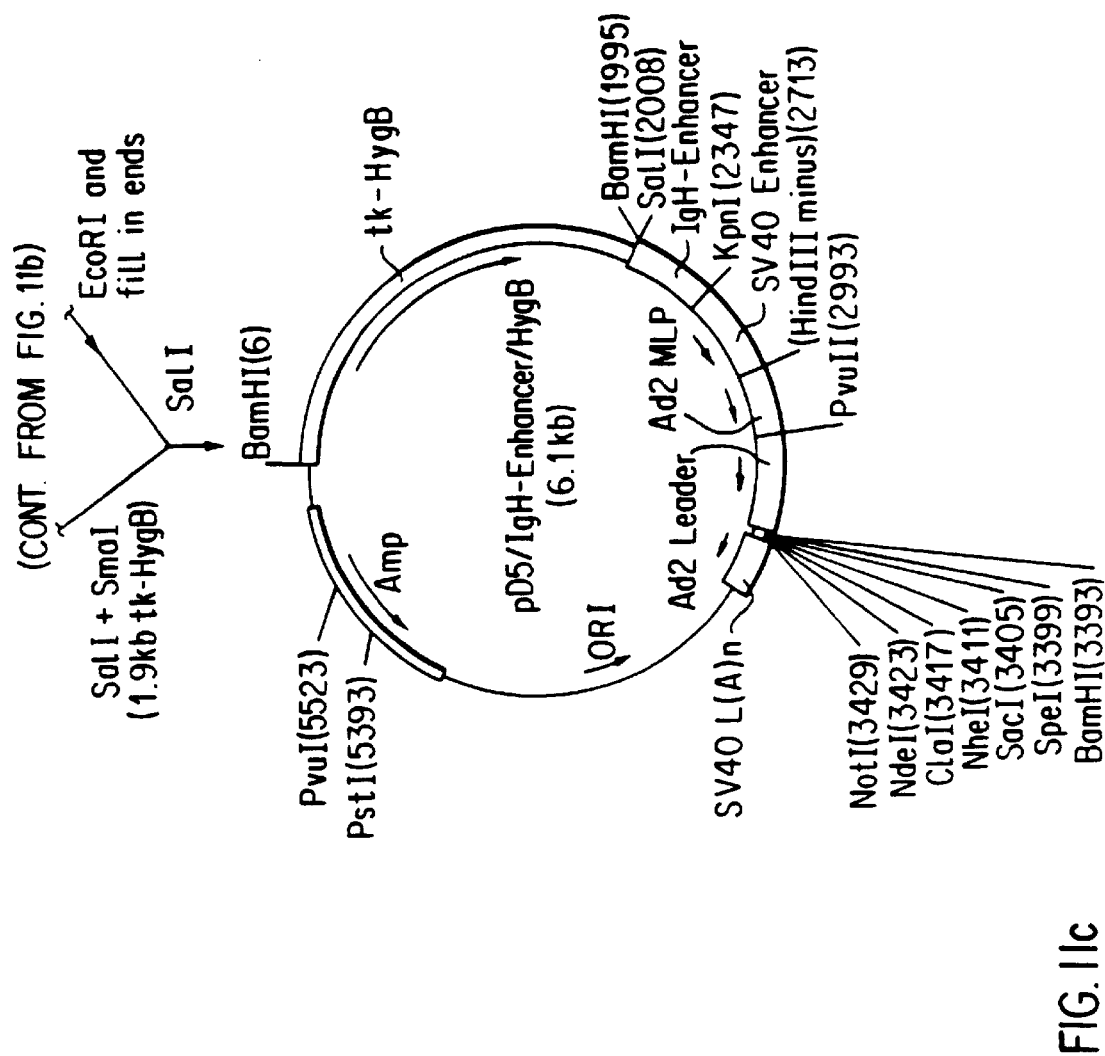

Expression vectors are defined herein as DNA sequences that are required for the transcription of cloned copies of genes and the translation of their mRNAs in an appropriate host. Such vectors can be used to express eukaryotic genes in a variety of hosts such as bacteria, blue-green algae, plant cells, yeast cells, insect cells and animal cells. The immunoglobulins may also be expressed in a number of virus systems. Specifically designed vectors allow the shuttling of DNA between host such as bacteria-yeast or bacteria-animal cells. An appropriately constructed expression vector should contain: an origin of replication for autonomous replication in host cells, selectable markers, a limited number of useful restriction enzyme sites, a potential for high copy number, and strong promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses. The heavy chain immunoglobulin molecule is transcribed from a plasmid carrying the neomycin (G418) resistance marker while the light chain immunoglobulin is transcribed from a plasmid carrying the hygromycin B resistance marker. With the exception of the drug resistance portion of these plasmids they are identical. The preferred progenitor of the immunoglobulin expression vectors is the pD5 (Berkner and Sharp, Nucl. Acids Res. 13: 841–857 [1985]) eukaryotic expression vector which contains the origin of adenovirus replication, the SV40 enhancer domain, the adenovirus major late promoter, the adenovirus 2 tripartite leader, a 5' splice donor from the adenovirus third leader and a 3' splice acceptor derived from an immunoglobulin locus, a multiple cloning site placed in the Bam H1 site subsequent to receipt of the vector, and the SV40 late polyadenylation signal (FIG. 10). The origin of replication is removed by digestion with Eco R1 and Kpn I and replaced by two fragments representing the neo selectable marker gene (derived from plasmid pCMVIE-AK1-DHFR as an Eco R1/Bam H1 about 1.8 Kb fragment) and the Ig heavy chain enhancer (obtained as a PCR amplified fragment using human DNA as the template, and the oligodeoxynucleotides listed in FIG. 4 as the primer pair, following its digestion with Bgl 11 and Kpn 1). The resultant expression vector is found to lack a small portion of the TK promoter responsible for the transcription of the neomycin gene. This is replaced by insertion into the Eco R1 site about a 0.14 Kb PCR amplified fragment derived from the CMVIE-AK1-DHFR DNA using the primer pair listed in FIG. 4. The resultant heavy chain expression vector (p8941) is modified by removal of the indicated Hind 111 and Xba I sites using standard procedures. To convert this vector into one expressing the hygromycin B selectable marker the neomycin-resistance cassette is removed by digestion first with Eco R1 followed by DNA polymerase-directed fill in of the 5' overhand, then subsequent Sal I digestion. The about 1.9 Kb hygromycin B expression cassette, TK promoter and TK polyadenylation signal flanking the hygromycin B gene, (obtained as a 1.8 kb Bam H1 fragment in plasmid pL690, Gritz and Davies, Gene 25: 179–188 [1981]) is removed from the plasmid pAL-2 by Bam H1 digestion and subcloned into the Bam H1 site of the intermediate vector pSP72. The hygromycin B cassette is removed from this vector by digestion with Sma I and Sal I and cloned into the expression vector linearized as described above to create a blunt end and Sal I end DNA fragment (FIG. 11).

Figure 7B:
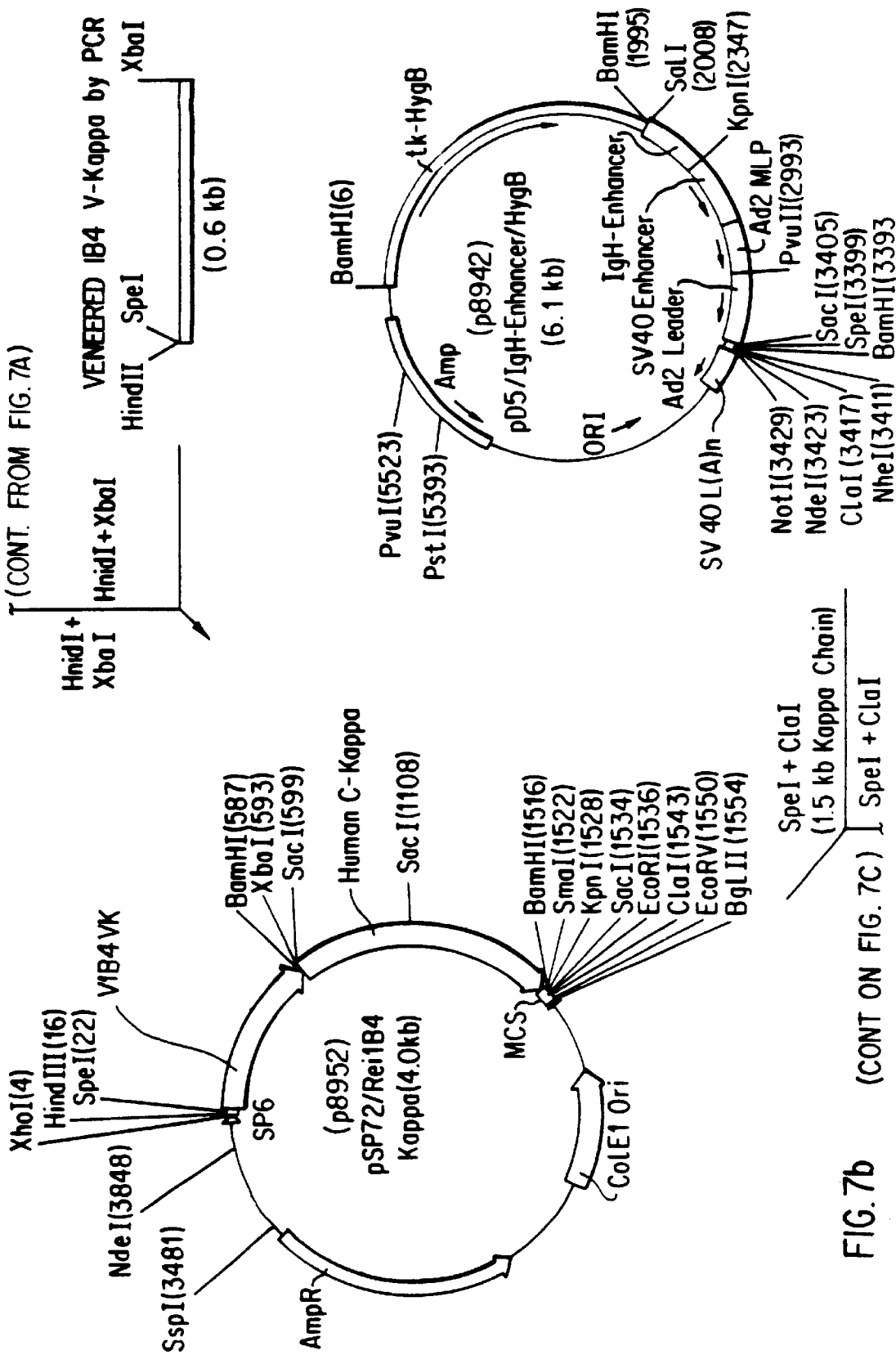
Figure 7C:
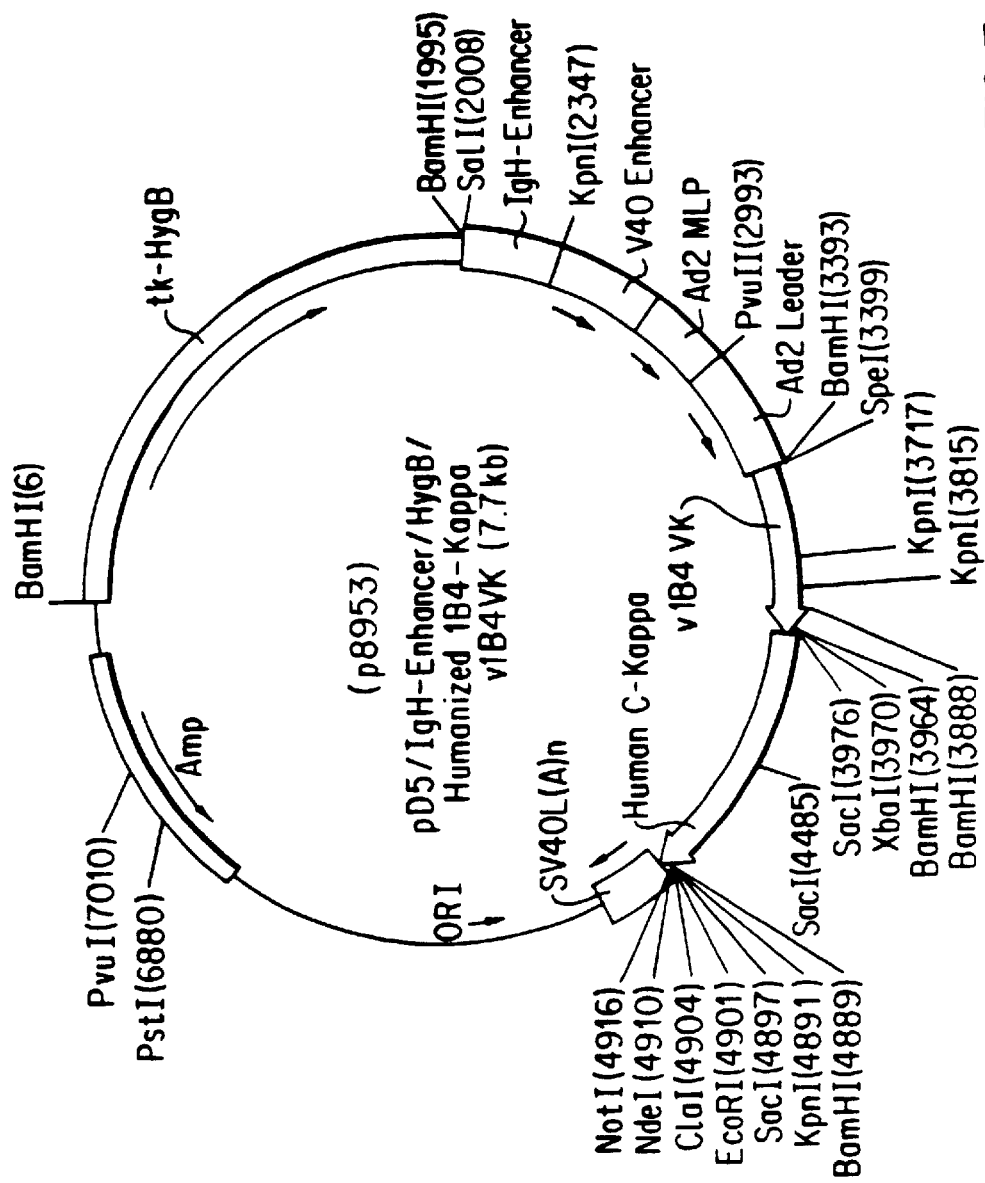

Expression of the 1B4 "veneered" kappa light chain is accomplished by transferring this cistron from the pSP72-based intermediate cloning vector (p8952), containing the human kappa constant region, to the hygromycin B selectable eukaryotic expression vector (FIG. 7). An about 1.5 kb DNA fragment resulting from the endonuclease digestion of p8952 with Spe I and Cla I is purified by agarose gel electrophoresis and ligated into the expression vector which has previously been linearized, following digestion with the same two restriction enzymes, and agarose gel purified. The heavy chain eukaryotic expression vector is constructed in two steps. First, the p8950 vector containing the modified heavy chain variable region of murine 1B4 fragment is digested with Bgl 11 and Bam H1. The agarose gel purified 0.75 kb fragment is ligated into the Bam H1 site of the p8941 vector and recombinant clones containing this fragment in the proper orientation are identified. Plasmid DNA from one such clone is linearized by Bam H1 digestion and ligated with a 1.78 Kb Bam H1 fragment representing a short version of the human gamma 4 constant region, derived from plasmid pAT84 by PCR amplification. Following the identification of clones containing these inserts in the appropriate orientation, plasmid DNAs (one which is referred to as p8953) are grown and purified for transfection into recipient mammalian cells.

Figure 13:
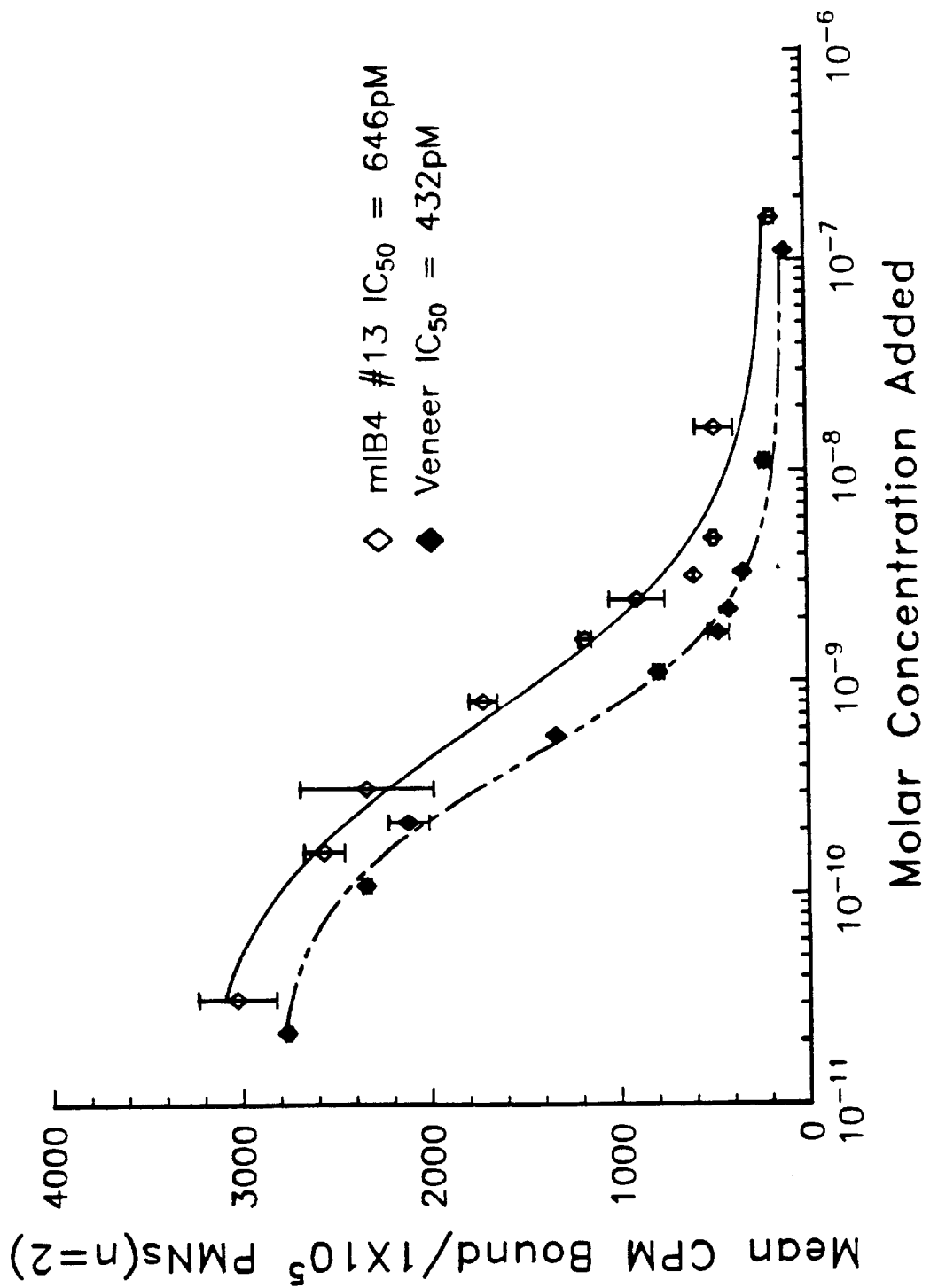
FIG. 13. Competitive binding assay of native murine 1B4 (open diamonds) and recombinant "veneered" 1B4 (closed diamonds).

Equal amounts, about 10 µg, of the plasmids encoding the 1B4 "veneered" IgG4 heavy chain and the 1B4 "veneered" kappa light chain are transfected by standard calcium phosphate precipitation procedures into the monkey kidney cell line CV-1P or the human embryonic kidney cell line 293. The culture supernants, assayed by a trapping ELISA (described below), were found to contain a human kappa light chain/human IgG4 immuno-globulin. Immulon-2 (Dynatech Labs.) 96-well plates are coated overnight with about a 5 µg/ml solution of mouse anti-human kappa chain constant domain monoclonal antibody (cat. #MC009, The Binding Site, Inc., San Diego, Calif.) in about 0.1 M $NaHCO_3$ buffer (pH 8.2) at about 4° C., and blocked with about 1% bovine serum (BSA) in about 0.1 M $NaHCO_3$ for about 1 hour at about 25° C. After this and all subsequent steps, washing was performed with phosphate buffered saline (PBS). The wells are then challenged with conditioned medium containing recombinant anti-CD18 antibody, or with predetermined quantities of human IgG4/kappa purified by protein A Sepharose (Pharmacia Fine Chemicals) chromatography from human IgG4 myeloma serum (cat. # BP026, The Binding Site, Inc.). All samples are diluted in PBS containing about 0.05% Tween-20. About 100 µl aliquots are incubated for about 1 hour at about 37° C. in triplicate, and standard calibration curves are constructed using IgG4 concentrations ranging from about 10 ng/ml to about 100 ng/ml. Bound and fully assembled human IgG4 (either native or the recombinant 1B4 human "veneered" IgG4 constructs) are detected with about 100 µl aliquots of a 1:500 dilution of mouse anti-human IgG4 Fc monoclonal antibody conjugated to alkaline phosphatase (cat #05-3822, Zymed Laboratories, Inc.) in phosphate buffered saline (PBS) containing about 1% BSA. After incubation for about 1 hour at about 37° C. and subsequent washing, the quantities of bound conjugate are detected by incubating all samples with a 1 mg/ml solution of p-nitrophenyl phosphate in 0.1 M 2,2' amino methyl-propanediol buffer, pH 10.3, for about 30 minutes at about 25° C. The adsorbance of the wells is determined with a UV Max ELISA plate reader (Molecular Devices) set at 405 nm. The antibody secreted by the transfected human 293 cells or monkey kidney CV1 P cells, either following transient expression or subsequent to stable clone isolation, is isolated by protein A chromatography, the concentration of recombinant human anti-CD18 antibodies determined by the trapping Elisa described above, and used to compete with the binding of radiolabeled murine 1B4 to the CD18 ligand on the surface of activated human PMNs. Affinities of r-anti-CD18 antibody constructs are determined using a competitive 125I-1 B4 soluble binding assay with stimulated human polymorpho-nuclear leukocytes (PMNs). Purified murine anti-CD18 monoclonal antibody (50 ug) is iodinated using chloramine-T (Hunter, W. M. and Greenwood, F. C., Nature 194: 495–496, 1962), and the radiolabeled antibody purified using a Bio-Sil TSK250 (Biorad, Richmond, Calif.) gel filtration HPLC column (which fractionates proteins in the range of 1–300×10³ daltons) equilibrated in 0.1 M phosphate buffer, pH 7.0. Effluent radioactivity is monitored with an in-line detector (Beckman Model 170; Beckman, Fullerton, Calif.) and total protein measured at OD280 with a Kratos Spectroflow 757 detector (Kratos, Mawah, N.J.). A single 125I-1B4 peak composed of coincident OD280 and radioactivity tracings characteristically elutes at about 6 minutes, 30 seconds following sample injection. Specific activity of the product is generally about 10 µCi/µg protein, and 97–99% of the counts are precipitable with 10% trichloroacetic acid. The binding of this radiolabeled antibody is assessed on human PMNs purified on a discontinuous Ficoll/Hypaque gradient (English, D. and Anderson, B. R., J. Immunol. Methods 5: 249–255, 1974) and activated with about 100 ng/ml phorbol myristate acetate for about 20 minutes at about 37° C. (Lo et al., J. Exp. Med. 169: 1779–1793, 1989). To determine the avidity of antibodies for CD18 molecules on the PMN surface, about $1 \times 10^5$ activated PMNs are incubated in a buffer such as Hanks balanced salt solution containing about 20 mM Hepes (pH 7.2), about 0.14 units aprotinin (Sigma Chemical Co.) and about 2% human serum albumin (binding buffer) containing about 1.3 ng 125I-1B4 (2.8×10-11 M) in the presence of increasing concentrations of unlabeled 1B4 antibody (about 10-7 to 10-15M) in about a 300 µl reaction volume for about 1 hour at about 4° C. with constant agitation. Cell bound 1B4 is separated from the unbound antibody by centrifugation through a 0.5 M sucrose cushion (4,800×g, 3 minutes); the tubes are frozen on dry ice, and the tips cut off and counted with an LKB gamma counter. The IC50 of the anti-CD18 antibody for the inhibition of 125I-1B4 antibody binding is calculated using a four parameter fitter program (Rodbard et al., In, "Radioimmunoassay and Related Procedures in Medicine", International Atomic Energy Agency, Vienna, vol 1, 469–504, 1978). The affinity of the "veneered" r-anti-CD18 antibody for the CD18 ligand is determined in a similar manner using murine 125I-1B4 antibody and increasing quantities, as determined by the trapping Elisa, of unlabeled r-anti-CD18. The results of the binding assays are shown in FIG. 13 and indicate that the avidity of the "veneered" recombinant 1B4 antibody is equal to that of the murine 1B4 monoclonal antibody. This result shows that an antibody with presumptive human isotype may be recombinantly constructed from the murine parent antibody by the introduction of numerous point mutations in its framework residues and expressed fused to human kappa and gamma 4 constant domains without loss in avidity for the antigen. It can be inferred from this result that the point mutations within the framework regions do not alter the presentation of the murine 1B4 light chain and heavy chain CDRs. Many of the examples of construction of recombinant human antibodies containing complementarity regions replaced by those found within murine monoclonal antibodies have resulted in loss of avidity for the ligand or antigen. Thus, although these latter transmutations are possible, the successful maintenance of avidity is not assured. This procedure described above demonstrates that when strict attention is payed to the framework regions, and the nature of the amino acids within each framework, "humanization" may potentially be achieved without the loss of avidity which accompanies the transfer of CDRs to the "generic" human frameworks ("humanization") employed by Winter, European Patent Publication No. 239,400, published Sep. 30, 1987.

To identify human framework sequences compatible with the CDRs of, say, murine 1B4, human frameworks with a high degree of sequence similarity to those of murine 1B4 are identified. Sequence similarity is measured using identical residues as well as evolutionarily conservative amino acid substitutions. Similarity searches are performed using the murine 1B4 framework sequence from which the CDR sequences had been removed. This sequence is used to query a database of human immunoglobulin sequences that had been derived from multiple sources. Sequences with a high degree of sequence similarity are examined individually for their potential as humanizing framework sequences. In this way, the human homologue providing the murine CDRs with the structure most similar to their native murine framework is selected as the template for the construction of the "veneered" variable regions (FIG. 12). Should human frameworks of sufficient similarity not be identifiable from compiled sequences, it is possible to isolate from human genomic DNA a group of closely related variable regions using recombinant technology. Thus, a degenerate 5' upstream oligodeoxynucleotide primer may be designed from the conserved sequences within the amino-terminus of each of the various human FR1 regions and paired with a degenerate 3' downstream oligodeoxynucleotide primers fashioned from the FR sequence determined from the murine monoclonal whose CDRs one wishes to transfer into a human context. These primer pairs are then used to PCR amplify from a human genomic template those DNA sequences which are flanked by the primer pair. The resulting DNAs may then be cloned and the DNA sequence derived from individual members will describe various murine-related human variable regions. The paucity of somatic mutations in framework residues and the conservation of amino acid sequence between mouse and man make this approach possible.

The construction of a complete recombinant human IgG4 antibody, whose heavy and light chain variable domains contain the CDR residues of the murine monoclonal antibody, with complete retention of the specificity and avidity of the parent murine monoclonal antibody is disclosed. The construction of the "veneered" light chain framework derived from the human sequence of LEN fused with a human kappa light chain constant region is described above. The murine variable region framework sequence, devoid of CDR sequences, is used to query a database of complete human variable region sequences. The human sequences that are most similar to the murine framework region are then analyzed individually to determine both their sequence identity and similarity to the murine framework region. In the case of murine 1B4 these sequences include, but are not limited to, "Gal", chosen because of its high degree of both similarity and identity with the 1B4 heavy chain sequence. The Gal FR has been found to be 85% similar and 79% identical-to murine 1B4. These values are based upon the Dayhoff similarity matrix of evolutionarily conserved amino acid substitutions (R. M. Schwartz, M. O. Dayhoff, in Atlas of Protein sequence and structure M. O. Dayhoff, Eds. (National Biomedical Research Foundation, Washington, DC [1979]) (FIG. 12). To prepare a recombinant DNA encoding the murine heavy chain CDRs in the context of a human-appearing framework the following procedures are performed. A set of ten short oligodeoxynucleotides are synthesized. Each pair is combined in a separate PCR reaction with the DNA template representing the murine 1B4 heavy chain variable region, amplified and isolated following PCR of the RNA of the murine hybridoma 1B4 as described above. Thus, about 50 pmole of each primer pair was combined with about 10 ng of plasmid DNA representing the murine 1B4 heavy chain variable region, about 2.5 units of Taq DNA polymerase and about twenty-five (25) cycles of PCR amplification ensued (cycle periods: 1', 94° C.; 1', 55° C.; 2' 72° C.). The products of the five reactions (FIG. 8) encoded portions of the 1B4 heavy chain variable region, beginning with the signal peptide encoding region and ending with the 3' intronic sequence which resides between the variable region coding domain and the IgG4 constant region sequence, with the desired point mutations to create a "veneered" variable region framework. These five fragments are purified by agarose gel electrophoresis, combined, about 10 ng of each DNA fragment, along with terminal oligodeoxynucleotide primers (A1 & A2, FIG. 5) and Taq DNA polymerase. The combined fragments were PCR amplified (25 cycles of: 2', 94° C.; 2', 55° C.; 2' 72° C.). By virtue of the complementary ends of the five fragments, the polymerization/-denaturation/ polymerization cycles of the polymerase chain reaction result in the formation, and subsequent amplification, of the combined sequences. Following 25 cycles of amplification the combined 0.8 Kb fragment is electrophoretically purified from an agarose gel and was digested with restriction enzymes Spe I and Bam H1. Following agarose gel electrophoresis, the purified DNA fragment is ligated into the heavy chain expression vector, p8958 (see FIG. 9), in place of the chineric variable region existing in this vector. Each "veneered" variable region, with its associated human constant region, residing within a pD5-based expression vector plasmid was co-transfected into 293 cells and CV1 P cells and recombinant human antibody is found to be present in the conditioned medium 48 hours post transfection. The "veneered" recombinant antibody is isolated by protein A chromatography. The avidity of this antibody for the CD18 ligand displayed on the surface of activated human PMNs is compared with that of the murine 1B4 monoclonal antibody parent. FIG. 13 shows that although each antibody contains the same set of six CDRs within different framework domains, they exhibit identical avidity for the ligand. Thus, the avidity of an antibody molecule does not rely upon the variable region framework residues which are surface exposed, rather the proper structure in which the CDRs are presented must be significantly influenced by the buried and inter/intra active residues. The parent murine monoclonal antibody demonstrates an $IC_{50}$ of about 1.0 to about 0.7 nM, the "veneered" molecule has a similar $IC_{50}$.

This invention further relates to a method of inhibiting the influx or migration of leukocytes capable of expressing CD18 antigen (leukocyte integrin, beta subunit) on their surface into a site of inflammation or a tissue area or organ that will become inflamed following an influx of the cells. The inflammation which is the target of the method of the present invention may result from an infection with pathogenic microorganisms such as gram-positive and gram-negative bacteria, parasites and fungi. The response may also be induced by viruses and non-infectious means such as trauma or reprefusion following myocardial infarction or stroke, immune responses to foreign antigen and autoimmune responses. The recombinant human anti-CD18 antibodies are useful in the treatment of inflammation in lung, central nervous system, kidney, joints, endocardium, eyes, ears, skin, gastrointestinal tract and urogenital system. Disease states in which the recombinant human anti-CD18 antibodies are useful as therapeutic agents include, but are not limited to: infectious diseases where active infection exists at any body site, such as meningitis; conditions such as chronic or acute secondary inflammations caused by antigen deposition; and other conditions such as, encephalitis; arthritis; uveitis; colitis; glomerulonephritis; dermatitis; psoriasis; and respiratory distress syndrome associated with sepsis and/or trama. Other inflammatory diseases which may be responsive to recombinant human anti-CD18 antibody include, but are not limited to, immune disorders and conditions involving T-cell and/or macrophage attachment/ recognition, such as acute and delayed hypersensitivity, graft vs. host disease; primary autoimmune conditions such as pernicious anemia; infection related autoimmune conditions such as Type I diabetes mellitis; flares during rheumatoid arthritis; diseases that involve leukocyte diapedesis, such as multiple sclerosis; antigen-antibody complex mediated diseases including certain of the secondary infection states listed above; immunosuppression; and transplant rejection. Inflammatory conditions due to toxic shock or trauma such as adult respiratory distress syndrome and reperfusion injury; and disease states due to leukocyte dyscrasias and metastasis, are included within the scope of this invention. The present invention is also applicable to the inhibition of leukocyte-endothelial attachment for diagnostic and therapeutic purposes; such as the iatrogenic opening of the endothelium to prevent the ingress of leukocytes during the ingress of a therapeutic drug in the instance of chemotherapy; or to enhance the harvesting of leukocytes from patients.

Recombinant human anti-CD18 antibodies or an active fragment thereof can be used to treat the above mentioned diseases. An active fragment will include the F(ab')2, the Fab and any other fragment that can bind to the CD18 antigen. Recombinant human anti-CD18 antibodies can be administered alone for non-infectious disease states or combined with antibiotics or other anti-infective agents for the treatment of infectious diseases for reasons discussed above. Administration will generally include the antibodies and possibly other substances in a physiologically acceptable medium or pharmaceutical carrier. Such physiologically acceptable media or pharmaceutical carriers include, but are not limited to, physiological saline, phosphate buffered saline, phosphate buffered saline glucose, buffered saline and the like. The antibodies and any anti-infective agent will be administered by parenteral routes which include intravenous, intramuscular, subcutaneous and intraperitoneal injection or delivery. The amount of the antibodies and the mixture in the dosage form is dependent upon the particular disease state being treated. The amount of the recombinant human anti-CD18 antibody utilized in a dosage form can range from about 1 to about 1,000 mg, with a range of from about 10 mg to about 100 mg being preferred. The antibodies can be administered daily or less than daily as determined by the treating physician. The following examples illustrate the present invention without, however, limiting the same thereto.

EXAMPLE 1
Preparation of a "Veneered" Recombinant Antibody

An antibody was produced in which the variable domain of the light chain comprises the framework region of a murine light chain modified to contain surface exposed amino acids of human derivation. The variable domain of the heavy chain is similarly derived from the murine heavy chain with point mutations which replace murine exposed residues with human-appearing residues. The light chain human framework region was derived from human myeloma protein LEN. The CDR and framework sequences from the murine monoclonal antibody 1B4 which binds to CD18 (the beta subunit of the leukocyte integrin B-2 family which includes: LFA-1, Mac-1, and p150.95) were derived as follows. The hybridoma designated 1B4 which produces 1B4 monoclonal antibody was deposited under the Budapest Treaty at the International Depository Authority: American Type Culture Collection, 10801 University Boulevard, Manassas, Va. 20110–2209. Viability was determined on Jun. 6, 1989 and the hybridoma was designated HB 10164. Previous experiments had determined this antibody to be an IgG 2a with a kappa light chain (Wright et al., Proc. Natl. Aca. Sci. USA 80: 5699–5703[1983]).

Total RNA was extracted from the 1B4 myeloma cells using standard methods involving cellular solubilization with guanidinium isothiocyanate (Chirgwin et al., Biochem. 18:5294–5299 [1979]). Sets of degenerate oligodeoxynucleotide primers (FIG. 4) representing sequences within framework 1 of the murine kappa light chain variable region and kappa light chain constant domain, or those within framework 1 of the murine IgG2a heavy chain variable region and heavy chain constant CH1 domain were synthesized by standard phosphoramidite procedures on an Applied Biosystem 381A DNA synthesizer. Removal of the oligodeoxynucleotides (oligos) from the resin was accomplished by treatment with concentrated $NH_4OH$ followed by desalting on a NAP-5 column (Pharmacia) with $H_2O$ elution (when the oligos were<45 bases in length), or by use of an OPC column (Applied Biosystems Inc) with 20% acetonitrile elution (when the oligos were>45 bases in length), as recommended by the manufacturers. Total RNA (2 $\mu$g) was reversed transcribed for 30' at 42° C. using Moloney MLV reverse transcriptase (200 units, BRL) and 10 pmoles of the constant region complementary strand primers representing either heavy or light chain in a buffer (final volume of 20 $\mu$l) containing 50 mM Tris HCl, pH 8.3,75 mM KCl, 3 mM $MgCl_2$, 10 mM DTT, and 20 units of RNAsin (Pharmacia). The reverse transcriptase was heat inactivated (95° C., 5') and the reactions were made to contain in 100 $\mu$l of PCR buffer (10 mM Tris HCl, pH 8.3, 50 mM KCl, 1.5 mM $MgCl_2$, 0.01% gelatin, 200 $\mu$M each dNTP), 50 pmoles of each of the paired primers, and 2.5 units of Taq polymerase (Perkin Elmer/Cetus). Polymerase chain reaction (PCR) amplification was carried out essentially as described by Saiki et al., *Science* 230: 1350–1354 (1985) and others (Mullis et al., *Cold Spring Harbor Symp. Quant. Biol.* 51: 263–273 [1986], Dawasaki and Wang, PCR Technology, Princples and Applications for DNA Amplification, Erlich, Ed., Stockton Press, NY, pp. 89–97 [1989], Tung et al., ibid. pp. 99–104 [1989]). Forty five cycles of amplification by a DNA Thermal Cycler (Perkin Elmer Cetus Instruments)(2', 94° C.; 2', 55° C.; 2' 72° C.) were followed by gel purification of the anticipated 400+base pair (bp) DNA fragments. Prior to subcloning the DNAs into a blunt-ended intermediate plasmid (pSP72, Promega) they were terminally phosphorylated using T4 polynucleotide kinase (Boehringer Mannheim). Multiple clones representing these PCR amplified sequences were isolated form DH5 transformed *E.coli* plated on LB agar plates containing 50 $\mu$g/ml ampicillin, grown by described procedures (Maniatis et al., *Molecular Cloning*, A Laboratory Manual, Cold Spring Harbor Laboratory, Cold Spring Harbor, N.Y., 1982), plasmid DNAs were extracted from the bacteria using the DNA preparation procedures of Birnboin and Doly, Nucleic Acid Res. 7: 1515 (1979), and the double-stranded plasmid DNAs were submitted to DNA sequence determinations using Sequenase® (United States Biochemicals) and T7 and SP6 specific sequencing primers (Boehringer Mannheim) using the protocols recommended by the manufacturer. A unique DNA sequence representing a murine IgG2a heavy chain variable region was obtained, as was a kappa light chain variable region sequence.

To give the final appearance of a "veneered" murine light chain, several residues within a template composed of the human LEN framework, into which had been grafted the CDRs described for 1B4, were replaced by corresponding residues found in the murine 1B4 light chain framework. Replacement of the human LEN variable region residues with those unique to MAb 1B4 took place as follows. Eight oligodeoxynucleotides (FIG. 5) were synthesized representing the primers necessary to generate by PCR amplification four DNA fragments. Incorporated into all but the terminal oligodeoxynucleotides were those sequences corresponding to the MAb 1B4 light chain variable region framework residues to be point mutated and at least 15 bases of 5'-terminal complementarity (see FIG. 6). The appropriate primer pair (50 pmole each) was combined with 10 ng of a 1B4 CDR-grafted LEN framework-containing plasmid DNA, 2.5 units of Taq DNA polymerase, PCR reaction components and buffer, and twenty-five (25) cycles of PCR amplification ensued (cycle periods: 1', 94° C.; 1', 55° C.; 2' 72° C.). The products of the four reactions, purified by agarose gel electrophoresis, were combined (10 ng of each DNA fragment) along with a terminal oligodeoxynucleotide primer pair (amplifier) (FIGS. 5 & 6), Taq DNA polymerase, PCR reaction components and buffer, and the subsequent recombined fragments were amplified, as described above, for twenty-five (see FIG. 6). Following restriction endonuclease digestion with HindIII and XbaI the amplified DNA was purified from an agarose gel and subcloned into these same sites of an intermediate vector pSP72 (Promega) which contained the human kappa light chain constant region, obtained as follows. DNA (1 µg) purified from a human B cell line (GM01018A; NIGMS Human Genetic Mutant Cell Repository, Institute for Medical Research, Camden, N.J. 08103) was used as a template for the oligodeoxynucleotide primers described in FIG. 4 to PCR amplify a 920 base pair fragment containing the splice acceptor for the human kappa light chain constant domain, the exon and a portion of its 3'-untranslated region (PCR primer pair choice was selected based on the kappa constant region sequence described by Hieter et al., Cell 22: 197–207 (1980). The PCR product was purified by agarose gel electrophoresis, digested with Bam H1 endonuclease, and subcloned into pSP72 (Promega) previously linearized with Bam H1.

The individual clones representing the pSP72 intermediate vector containing both the 1B4 "veneered" light chain variable region derived as described above, and the human kappa constant region, derived by PCR amplification of human DNA, were used to verify the DNA sequence of the "veneered" light chain variable region. The "veneered" heavy chain portion of the recombinant antibody was derived from a point mutated murine 1B4 heavy chain variable region fused to the human constant region of gamma 4 subtype obtained from a lambda library constructed by Flanagan and Rabbitts, Nature 300: 709–713 (1982).

The variable region of the "veneered" heavy chain was constructed from five DNA fragments representing a signal sequence, mutated portions of the murine 1B4 heavy chain variable region, and an intronic sequence (FIG. 8). Oligodeoxy-nucleotide primer pairs (FIG. 5) were synthesized representing the primers necessary to generate by PCR amplification these five DNA fragments from 10 ng of plasmid DNA template containing the murine 1B4 heavy chain variable region previously used to determine the murine 1B4 CDR and framework sequences. Amplification of the five fragments was performed as described above for the four light chain variable region fragments. The agarose gel purified products were combined (10 ng of each product) with terminal primer pairs (FIG. 5) and the PCR-generated in vitro recombined template was amplified using the standard procedure also described above for recombining the fragments comprising the "veneered" light chain variable region. Prior to subcloning into a Hind III and Bam HI digested expression vector this recombined product was similarly digested and agarose gel purified. DNA was obtained following growth of individual bacterial clones and submitted to DNA sequence determination using Sequenase® and T7 and SP6 specific sequencing primers in order to verify the sequence of the reconstructed variable region and its flanking domains.

The gamma 4 heavy chain constant region had been subcloned as a 6.7 Kb Hind III fragment derived from the plasmid pAT84 (Flanagan and Rabbitts, supra) into the Hind III site of the intermediate vector pSP72 (Promega). This plasmid was then used as the template DNA from which a shortened version of the gamma 4 constant region was obtained using the standard PCR amplification procedures described above and the primer pairs indicated in FIG. 4. Eukaryotic expression vectors were constructed as described below such that the heavy chain immunoglobulin molecule was transcribed from a plasmid carrying the neomycin (G418) (Rothstein and Reznikoff, Cell 23: 191–199 [1981]) resistance marker, while the light chain immunoglobulin was transcribed from a plasmid carrying the hygromycin B resistance marker (Gritz and Davies, Gene 25: 179–188 [1983]). With the exception of the drug resistance portion of these plasmids they are identical.

The progenitor of the immunoglobulin expression vectors was the pD5 eukaryotic expression vector (Berkner and Sharp, Nucl. Acids Res. 13: 841–857 [1985]) which contained the origin of adenovirus replication, the SV40 enhancer domain, the adenovirus major late promoter, the adenovirus 2 tripartite leader, a 5' splice donor from the adenovirus third leader and a 3' splice acceptor derived from an immunoglobulin locus, a multiple cloning site, and the SV40 late polyadenylation signal (FIG. 10). The origin of replication was removed by digestion with Eco R1 and Kpn I and replaced by two fragments representing the neo selectable marker gene (derived from plasmid pCMVIE-AK1-DHFR (Silberklang et al, *Modern Approaches to Animal Cell Technology,* Ed. Spier et al., Butterworth, U.K., [1987]) as an Eco R1/Bam H1 1.8 Kb fragment) and the Ig heavy chain enhancer (obtained as a PCR amplified fragment using standard procedures described above and human DNA as the template; the oligodeoxynucleotide primer pair is listed in FIG. 4) following its digestion with Bgl II and Kpn I. The resultant expression vector was found to lack a small portion of the TK promoter responsible for the transcription of the neomycin gene. This was replaced by insertion into the Eco RI site of a 0.14 kb PCR amplified fragment derived from the CMVIE-AK1-DHFR DNA using the primer pair also listed in FIG. 4. The resultant heavy chain expression vector was subsequently modified by removal of the indicated Hind III and Xba I sites. To convert this neomycin selectable vector into one expressing the hygromycin B selectable marker (FIG. 11) the neomycin-resistance cassette was removed by digestion first with Eco R1 followed by DNA polymerase-directed fill in of the 5' overhang, then subsequent Sal I digestion. The 1.9 kb hygromycin B expression cassette [TK promoter and TK polyadenylation signal flanking the hygromycin B gene obtained from Gritz and Davies, Gene 25: 179–188 (1983), as the 1.9 kb Bam H1 fragment in plasmid (pLG90)] was removed from the plasmid pAL-2 by Bam H1 digestion and subcloned into the Bam H1 site of the intermediate vector pSP72 (Promega). The hygromycin B cassette was removed from this vector by digestion with Sma I and Sal I and cloned into the expression vector linearized as described above to create a blunt end and Sal I end DNA fragment.

Expression of the 1B4 "veneered" kappa light chain was accomplished by transferring this cistron from its position within the pSP72 intermediate vector to the hygromycin B selectable eukaryotic expression vector (FIG. 7). A 1.5 kb DNA fragment resulting from the endonuclease digestion of v1B4 VK/pSP72 intermediate vector with Spe I and Cla I was purified by agarose gel electro-phoresis and ligated into the expression vector which had previously been linearized, by digestion with the same two restriction enzymes and agarose gel purified.

Figure 9A:
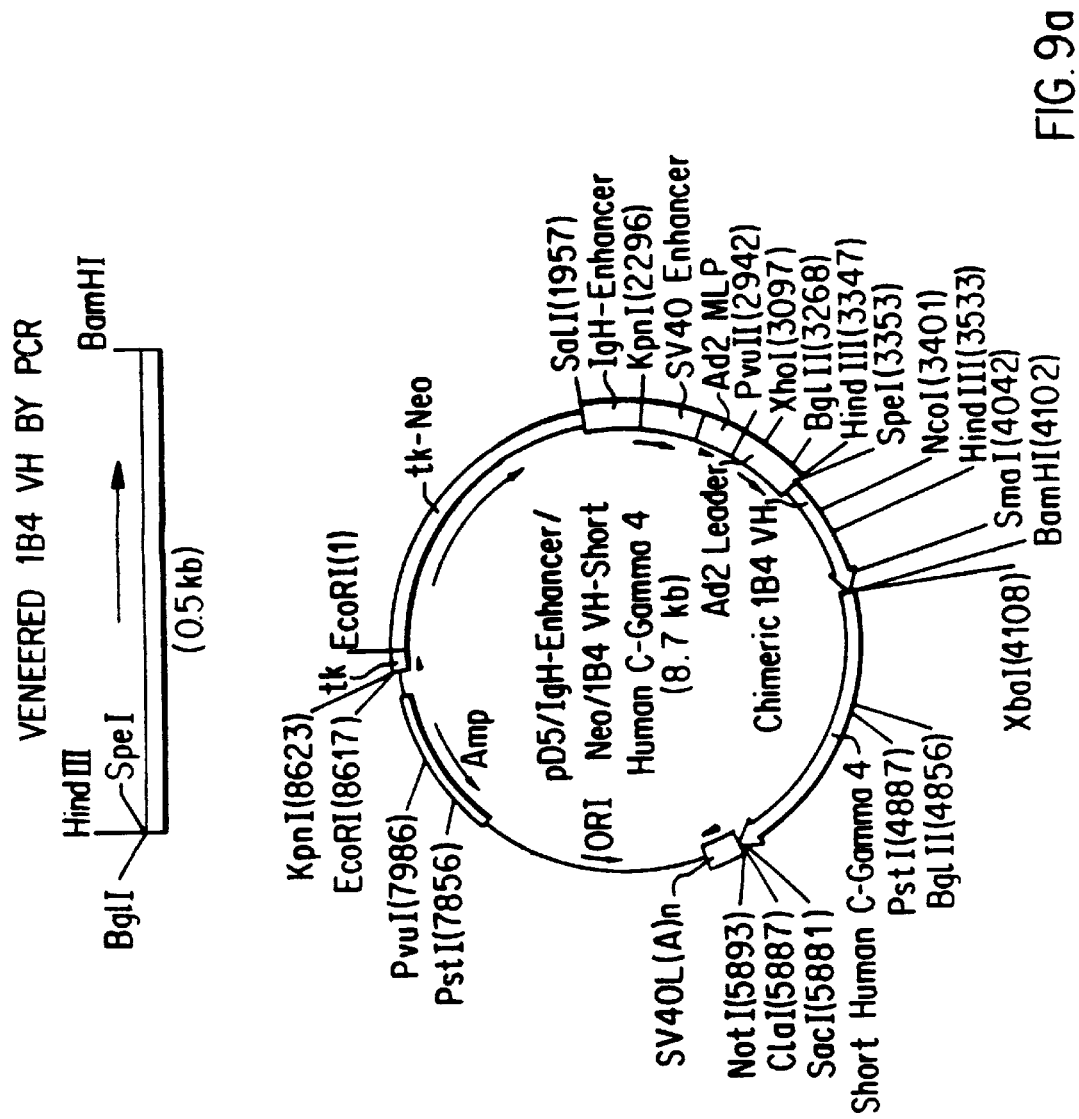
FIGS. 9A an 9B. Outline of the insertion of the "veneered" heavy chain variable region into the heavy chain expression vector.
Figure 9B:
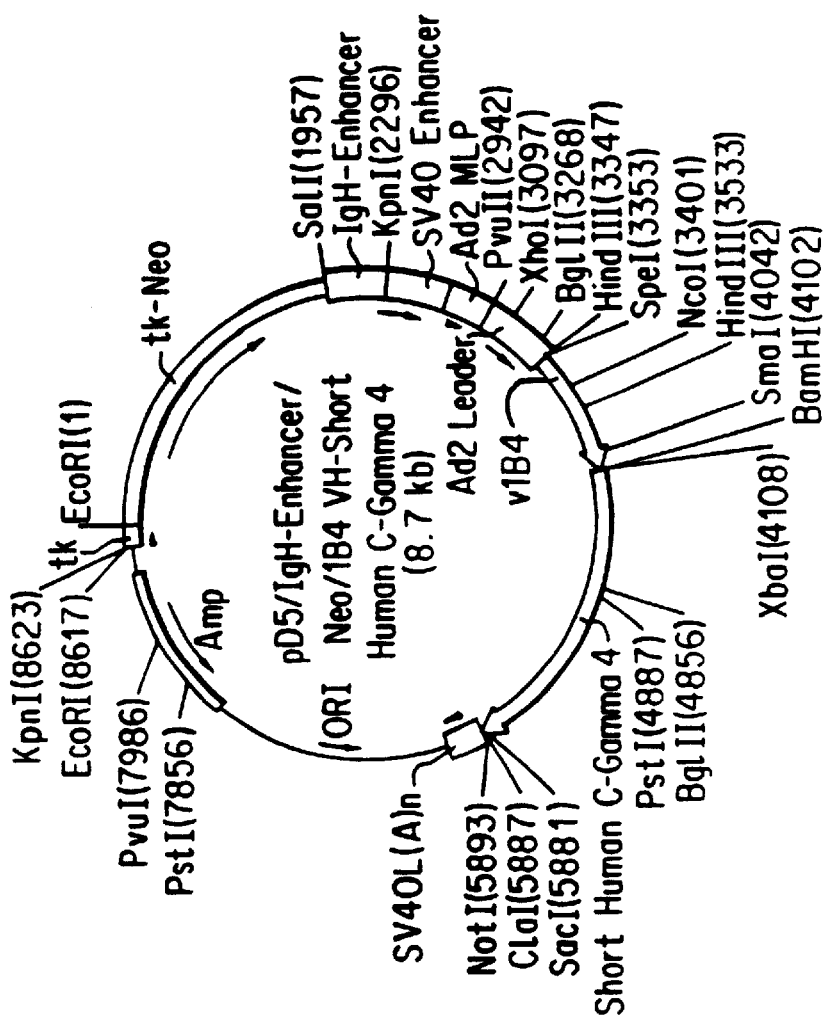

The 1B4 "veneered" heavy chain eukaryotic expression vector was constructed in one step (FIG. 9) from an existing vector previously constructed to express a chimaeric form of the 1B4 heavy chain. The "veneered" heavy chain variable region created by PCR amplifcation (FIG. 8) was digested with Hind III and Bam H1. The agarose gel purified 0.8 kb fragment was ligated into the Hind III and Bam H1 sites of the pD5/IgH-Enhancer/Neo/1B4 VH-Short Human C-Gamma 4 expression vector following its endonuclease digestion with these two enzymes and subsequent purification by agarose gel electrophoresesis (FIG. 9). Transformants containing both variable and constant regions were identified. Plasmid DNAs were grown (Maniatis et al., supra) and purified for transfection into recipient mammalian cells (Maniatis et al., supra; Birbion and Doly, supra.).

Equal amounts (10 $\mu$g) of the plasmids encoding the "veneered" IgG4 heavy chain and the "veneered" kappa light chain were transfected by standard calcium phosphate precipitation procedures into human 293 cells and african green monkey kidney CV-1P cells. The culture supernatant fluids were assayed by a trapping Elisa (described below) for the secretion of a human kappa light chain containing IgG4 immunoglobulin.

An Elisa was developed for the quantitation of the amounts of a 1B4 recombinant antibody expressed in conditioned mammalian cell growth medium. Immulon-2 (Dynatech Labs.) 96-well plates are coated overnight with a 5 $\mu$g/ml solution of mouse anti-human k chain constant domain monoclonal antibody (cat. #MC009, The Binding Site, Inc., San Diego, Calif.) in 0.1M NaHCO$_3$ buffer (pH 8.2) at 4° C., and blocked with 1% bovine serum (BSA) in 0.1M NaHCO$_3$ for 1 h at 25° C. After this and all subsequent steps, washing was performed with phosphate buffered saline (PBS). The wells are then challenged with conditioned medium containing recombinant anti-CD18 antibody, or with predetermined quantities of human IgG4 purified by protein A Sepharose (Pharmacia Fine Chemicals) chromatography from human IgG4 myeloma serum (cat. # BP026, The Binding Site, Inc.). All samples are diluted in PBS containing 0.05% Tween-20. 100 $\mu$l aliquots are incubated for 1h at 37° C. in triplicate, and standard calibration curves are constructed using IgG4 concentrations ranging from 10 ng/ml to 100 ng/ml. Bound and fully assembled human IgG4 (either native or recombinant "veneered"1B4 human IgG4 constructs) are detected with 100 $\mu$l aliquots of a 1:500 dilution of mouse anti-human IgG4 Fc monoclonal antibody conjugated to alkaline phosphatase (cat #05-3822, Zymed Laboratories, Inc.) in phosphate buffered saline (PBS) containing 1% BSA. After incubation for 1 h at 37° C. and subsequent washing, the quantities of bound conjugate are detected by incubating all samples with a 1 mg/ml solution of p-nitrophenyl phosphate in 0.1M 2,2'amino-methyl-propanediol buffer, pH 10.3, for 30 min at 25° C. The adsorbance of the wells is determined with a UV Max ELISA plate reader (Molecular Devices) set at 405 nm. All supernatant fluids contain this immunoglobulin, though in various amounts. The antibody secreted by the transfected 293 cells is concentrated by protein A chromatography and the concentrations of the recombinant human "veneered" anti-CD18 antibody determined by the trapping Elisa described above, is used to compete with the binding of radiolabeled murine 1B4 to the CD18 ligand on the surface of activated human PMNs. Affinities of various anti-CD18 antibody constructs are determined using a competitive 125I-m1B4 soluble binding assay with stimulated human polymorphonuclear leukocytes (PMNs). Purified murine anti-CD18 monoclonal antibody (50 ug; m1B4) is iodinated using chloramine-T (Hunter, W. M. and Greenwood, F. C., Nature 194: 495–496, 1962), and the radiolabeled antibody purified using a Bio-Sil TSK250 (Biorad, Richmond, Calif.) gel filtration HPLC column (which fractionates proteins in the range of 1–300×103 daltons) equilibrated in 0.1M phosphate buffer, pH 7.0. Effluent radioactivity is monitored with an in-line detector (Beckman Model 170; Beckman, Fullerton, Calif.) and total protein measured at OD280 with a Kratos Spectroflow 757 detector (Kratos, Mawah, N.J.). A single 125I-m1B4 peak composed of coincident OD280 and radioactivity tracings characteristically elutes 6 minutes, 30 seconds following sample injection. Specific activity of the product is generally about 10 $\mu$Ci/$\mu$g protein, and 97–99% of the counts are precipitable with 10% trichloroacetic acid. The binding of this radiolabeled antibody is assessed on human PMNs purified on a discontinuous Ficoll/Hypaque gradient (English, D. and Anderson, B. R., J. Immunol. Methods 5: 249–255, 1974) and activated with 100 ng/ml phorbol myristate for 20 minutes at 37° C. (Lo et al., *J. Exp. Med.* 169: 1779–1793, 1989). To determine the avidity of antibodies for CD18 molecules on the PMN surface, about 1×10$^5$ activated PMNs are incubated in a buffer such as Hanks balanced salt solution containing 20 mM Hepes (pH 7.2), 0.14 units aprotinin (Sigma Chemical Co.) and 2% human serum albumin (binding buffer) containing 1.3 ng 125I-m1B4 (2.8×10-11M) in the presence of increasing concentrations of unlabeled m1B4 antibody (10–7 to 10–15M) in a 300 ul reaction volume for about 1 h at about 4° C. with constant agitation. Cell bound 1B4 is separated from the unbound antibody by centrifugation through a 0.5M sucrose cushion (4,800×g, 3 minutes); the tubes are frozen on dry ice, and the tips cut off and counted with an LKB gamma counter. The IC50 of the anti-CD18 antibody for the inhibition of 125I-m1B4 antibody binding is calculated using a four parameter fitter program (Rodbard, D, Munson, P. J., and DeLean, In, "Radioimmunoassay and Related Procedures in Medicine", International Atomic Energy Agency, Vienna, vol I, 469–504, 1978). The affinity of the "veneered" anti-CD18 antibody for the CD18 ligand is determined in a similar manner using murine 125I-m1B4 antibody and increasing quantities, as determined by the trapping Elisa, of unlabeled "veneered" anti-CD18 antibody. The results of the binding assays are shown in FIG. 13 and indicate that the avidity of the "veneered" heavy chain and light chain recombinant 1B4 antibody is equivalent to that of the murine 1B4 monoclonal antibody.

The "veneered" heavy and light chain expression vectors were co-transfected into CV1P monkey kidney cells using 20 $\mu$g of each plasmid to prepare 2 mL of the calcium phosphate precipitated solution. One mL was placed in the medium overlaying each 100 mm dish of CV1P cells. After 4 hr at 37° C. the medium was replaced with 1 mL of 15% glycerol in 1×HBS (Hepes buffered salt). Following the 3 min glycerol shock, 10 mL of PBS as added, the cell monolayers were aspirated, washed once with 10 mL of PBS, and re-fed with fresh medium (DMEM+10% heat inactivated new born calf serum) containing 200 $\mu$g of hygromycin B and 800 μg of G418 per mL. Cloning cylinders (Fishney, In, Culture of Animal Cells, Alan R. Liss, Inc. New York, 1983) were used to isolate individual colonies prior to their expansion and subsequent assay for productivity. Two clones, #11 and #48, were found to express sufficient amounts of v1B4 to warrant their expansion and ultimate accessioning.

EXAMPLE 2

Immunogenicity of a Veneered Murine Antibody Molecule

Figure 14:
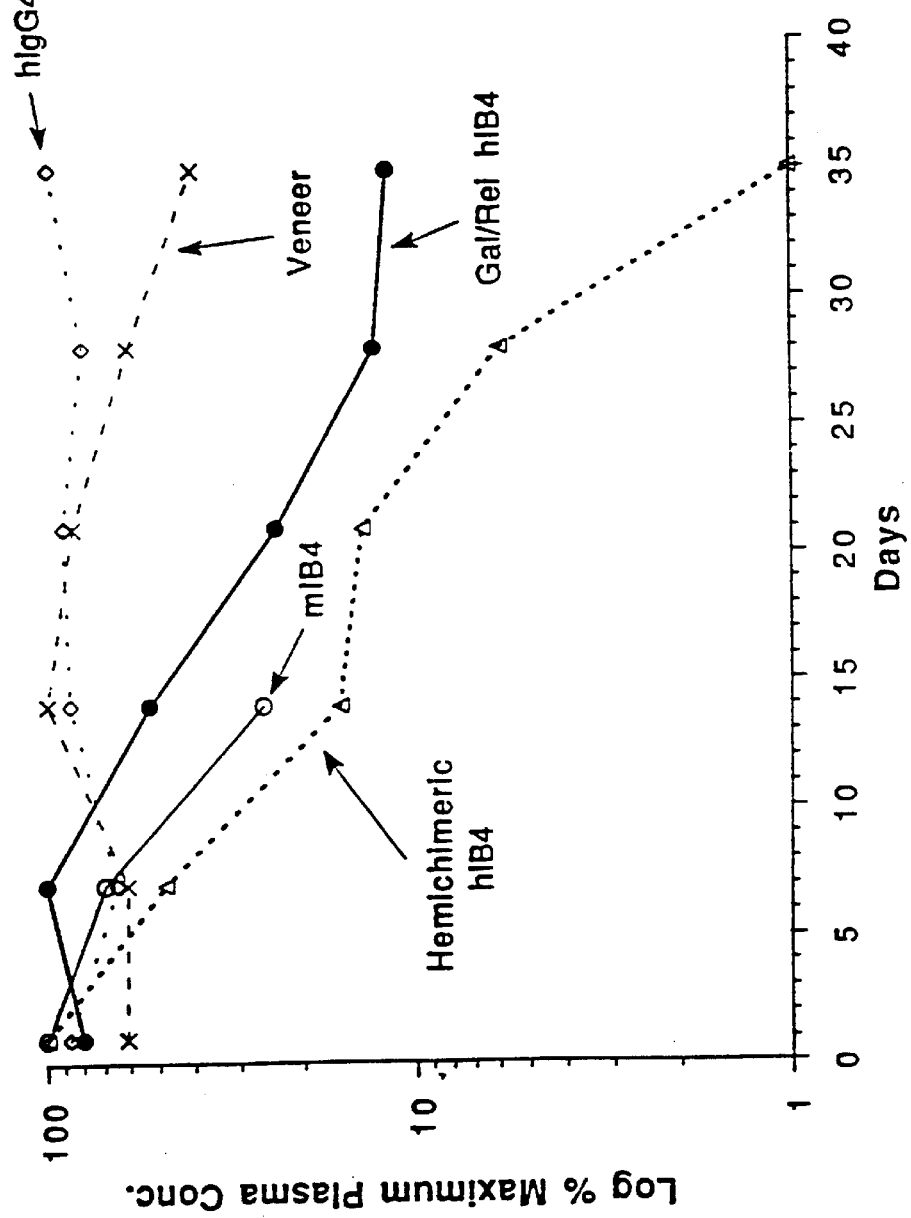
FIG. 14. Inmunogenicity of a veneered murine antibody in Rhesus monkeys is shown.

Human MAbs have been found to have the same pharmacokinetics in Rhesus monkeys as they do in humans. After repeated dosing of human MAbs into these monkeys they were well tolerated and rarely resulted in immune recognition. Groups of three Rhesus monkeys were injected, at weekly intervals, for five weeks with one milligram of MAb (either murine, CDR-grafted, Hemi-chimeric, or Veneered) per kilogram body weight. At various times following each injection the level of circulating MAb and the development of anti-MAb antibodies were assayed by ELISAs. The IB4 MAbs all bound their CD18 target on Rhesus PMNs and serum half-lives were initially about three to four hours. This value predominantly reflects the normal rapid turnover rate of the PMN population. Differences between the humanized versions of IB4 and its murine predecessor were appreciated by the third dose of antibody when two of the three monkeys receiving the murine antibody displayed moderate anaphylactic symptoms. This response was never seen in animals treated with the other forms of the IB4 MAb during the six weeks of this study. Distinguishing differences between the recombinant IB4 MAbs were most evident following their fourth dose at which time peak plasma levels for the CDR-grafted MAbs (Hemi-chimeric and fully CDR-grafted) were significantly reduced relative to the Veneered MAb. This trend continued for the remainder of the observation period (FIG. 14) and could be attributed to the progressively higher levels of anti-IB4 antibodies in these animals. These findings show that a veneering approach to humanization may not only result in recombinant antibodies which retain all of their affinity and potency, but these antibodies may also be less immunogenic than those humanized by CDR-grafting and reshaping procedures.

What is claimed is:

1. A method of producing a veneered immunoglobulin having the ligand binding properties of an immunoglobulin from a first mammalian species and having the immunogenic properties of reduced immunogenicity in a second mammalian species, the process comprising:
   a) comparing a variable domain of the first species immunoglobulin with variable domains of immunoglobulins from the second species at corresponding framework amino acid sequences;
   b) selecting from the variable domains of the second species immunoglobulins the variable domain which is most similar to the variable domain of the first species immunoglobulin at corresponding framework amino acid sequences;
   c) identifying framework amino acid residues of the first species variable domain which differ from the amino acid residues at the corresponding position of the selected variable domain, these differing amino acid residues being limited to those determined to be exposed to solvent, which are not directly adjacent to a complementarity determining region; and
   d) producing an immunoglobulin having the first species variable domain with only the identified amino acid residues identified in step c) being replaced with the corresponding residues present in the selected variable domain.

2. The method of claim 1 wherein the first mammalian species is mouse.

3. The method of claim 1 wherein the second mammalian species is human.

* * * * *

SEQUENCE LISTING (1) GENERAL INFORMATION:

(iii) NUMBER OF SEQUENCES: 38

(2) INFORMATION FOR SEQ ID NO: 1:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

TCTCGGATCC GAYATYGTGM TSACCCAR                              28

(2) INFORMATION FOR SEQ ID NO: 2:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

TCTCAAGCTT TGGTGGCAAG ATRGATACAG TTGGTGCAGC              40

(2) INFORMATION FOR SEQ ID NO: 3:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 3:

TTCTGGATCC SAGGTBCARC TGMAGSAGTC WGG                      33

(2) INFORMATION FOR SEQ ID NO: 4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

TTCTGGATCC SAGGTBAAGC TGGTGSAGTC WGG                                            33

(2) INFORMATION FOR SEQ ID NO: 5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

TCTCAAGCTT ACCGATGGRG CTGTTGTTTT GGC                                            33

(2) INFORMATION FOR SEQ ID NO: 6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

ATTTGGATCC TCTAGACATC GCGGATAGAC AAGAAC                                     36

(2) INFORMATION FOR SEQ ID NO: 7:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

AATAATGCGG CCGCATCGAT GAGCTCAAGT ATGTAGACGG GGTACG                 46

(2) INFORMATION FOR SEQ ID NO: 8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

TATAGAATTC GGTACCCTTC ATCCCCGTGG CCCG                                           34

(2) INFORMATION FOR SEQ ID NO: 9:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

TGCGTGTTCG AATTCGCC                                                          18

(2) INFORMATION FOR SEQ ID NO: 10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

TTTTAGATCT GTCGACAGAT GGCCGATCAG AACCAG                                      36

(2) INFORMATION FOR SEQ ID NO: 11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

TTGGTCGACG GTACCAATAC ATTTTAGAAG TCGAT                                       35

(2) INFORMATION FOR SEQ ID NO: 12:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

TCTCGGATCC TCTAGAAGAA TGGCTGCAAA GAGC                                        34

(2) INFORMATION FOR SEQ ID NO: 13:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

TCTCGCTAGC GGATCCTTGC AGAGGATGAT AGGG                                        34

(2) INFORMATION FOR SEQ ID NO: 14:

(i) SEQUENCE CHARACTERISTICS:
        (A) LENGTH: 50 base pairs
        (B) TYPE: nucleic acid
        (C) STRANDEDNESS: single
```

```
        (D) TOPOLOGY: linear (ii) MOLECULE TYPE: cDNA (xi) SEQUENCE DESCRIPTION: SEQ ID NO: 14:

CATTCGCTTA CCAGATCTAA GCTTACTAGT GAGATCACAG TTCTCTCTAC            50

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

TGGCTCTGCA GCTGATGGTG                                            20

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

CACCATCAGC TGCAGAGCCA                                            20

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

CTGTCTGGGA TCCCAGATTC                                            20

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

GAATCTGGGA TCCCAGACAG                                            20

(2) INFORMATION FOR SEQ ID NO: 19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO: 19:

GTTGCAACAT CTTCAGCCTC CACGCTGCTG ATG                                            33

(2) INFORMATION FOR SEQ ID NO: 20:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 20:

GTGGAGGCTG AAGATGTTGC AACTTATTAC TG                                             32

(2) INFORMATION FOR SEQ ID NO: 21:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 21:

GAATGTGCCT ACTTTCTAGA GGATCCAACT GAGGAAGCAA AG                                  42

(2) INFORMATION FOR SEQ ID NO: 22:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 22:

CATTCGCTTA CCAGATCT                                                             18

(2) INFORMATION FOR SEQ ID NO: 23:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 23:

GAATGTGCCT ACTTTCTAG                                                            19

(2) INFORMATION FOR SEQ ID NO: 24:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 24:

CCCTCCAGGC TTCACTAAGT CTCCCCC                                                   27

(2) INFORMATION FOR SEQ ID NO: 25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

```
TTAGTGAAGC CTGGAGGGTC CCTGAAACTC                                    30
```

(2) INFORMATION FOR SEQ ID NO: 26:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

```
GCCCCTTCCC AGGAGCTTGG CGAACCCAAG ACATG                              35
```

(2) INFORMATION FOR SEQ ID NO: 27:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

```
AAGCTCCTGG GAAGGGGCTG GAGTTGGTCG CAGCC                              35
```

(2) INFORMATION FOR SEQ ID NO: 28:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

```
TGTTCATTTG TAGGTACAGG GTGTTCTTGG AATTGTCTCT GGAGATGGTG              50
```

(2) INFORMATION FOR SEQ ID NO: 29:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

```
TGTACCTACA AATGAACAGT CTGAGGGCTG AGGACACAGC CTTGTATT                48
```

(2) INFORMATION FOR SEQ ID NO: 30:

(i) SEQUENCE CHARACTERISTICS:

(A) LENGTH: 29 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 30:

CTGTGAGAAG GGTGCCTTGG CCCCAGTAG                                29

(2) INFORMATION FOR SEQ ID NO: 31:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 31:

AAGGCACCCT TCTCACAGTC TCCTCAGGTG                               30

(2) INFORMATION FOR SEQ ID NO: 32:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 32:

GAATGTGCCT ACTTAAGCTT TCTAGAGGAT CCTATAAATC TCTGGCCATG         50

(2) INFORMATION FOR SEQ ID NO: 33:

(i) SEQUENCE CHARACTERISTICS:
       (A) LENGTH: 120 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 33:

Asp Val Lys Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Leu Val
         35                  40                  45

Ala Ala Ile Asp Asn Asp Gly Gly Ser Ile Ser Tyr Pro Asp Thr Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                85                  90                  95

Ala Arg Gln Gly Arg Leu Arg Asp Tyr Phe Asp Tyr Trp Gly Gln
            100                 105                 110

Gly Thr Leu Leu Thr Val Ser Ser
         115                 120

(2) INFORMATION FOR SEQ ID NO: 34:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

```
Asp Val Lys Leu Val Glu Ser Gly Gly Asp Leu Val Lys Leu Gly Gly
 1               5                  10                  15
Ser Leu Lys Leu Ser Cys Ala Ala Ser Gly Phe Thr Phe Ser Asp Tyr
            20                  25                  30
Tyr Met Ser Trp Val Arg Gln Thr Pro Glu Lys Arg Leu Glu Leu Val
        35                  40                  45
Ala Ala Ile Asp Asn Asp Gly Ser Ile Ser Tyr Pro Asp Thr Val
    50                  55                  60
Lys Gly Arg Phe Thr Ile Ser Arg Asp Asn Ala Lys Asn Thr Leu Tyr
65                  70                  75                  80
Leu Gln Met Ser Ser Leu Arg Ser Glu Asp Thr Ala Leu Tyr Tyr Cys
                85                  90                  95
Ala Arg Gln Gly Arg Leu Arg Arg Asp Tyr Phe Asp Tyr Trp Gly Gln
                100                 105                 110
Gly Thr Thr Leu Thr Val Ser Ser
                115                 120
```

(2) INFORMATION FOR SEQ ID NO: 35:

(i) SEQUENCE CHARACTERISTICS:
        (A) LENGTH: 115 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

```
Glu Val Gln Leu Val Glu Ser Gly Gly Asp Leu Val Gln Pro Gly Arg
 1               5                  10                  15
Ser Leu Arg Leu Ser Cys Ala Ala Ser Gly Phe Thr Phe Ser Asx Leu
            20                  25                  30
Gly Met Thr Trp Val Arg Gln Ala Pro Gly Lys Gly Leu Glu Trp Val
        35                  40                  45
Ala Asn Ile Lys Glx Asx Gly Ser Glx Glx Asx Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Val Glu Asp Thr Ala Leu Tyr Tyr Cys
                85                  90                  95
Ala Arg Gly Trp Gly Gly Asp Trp Gly Gln Gly Thr Leu Val Thr
                100                 105                 110
Val Ser Thr
     115
```

(2) INFORMATION FOR SEQ ID NO: 36:

(i) SEQUENCE CHARACTERISTICS:
        (A) LENGTH: 112 amino acids
        (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO: 36:

Asp Ile Val Met Thr Gln Ser Ser Asn Ser Leu Ala Val Ser Leu Gly
1               5                  10                  15

Glu Arg Ala Thr Ile Ser Cys Arg Ala Ser Glu Ser Val Asp Ser Tyr
                20                  25                  30

Gly Asn Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Asp
        50                  55                  60

Arg Phe Ser Gly Ser Gly Ser Gly Thr Asp Phe Thr Leu Thr Ile Ser
65                  70                  75                  80

Ser Val Glu Ala Glu Asp Val Ala Thr Tyr Tyr Cys Gln Gln Ser Asn
                85                  90                  95

Glu Asp Pro Leu Thr Phe Gly Gln Gly Thr Lys Leu Glu Ile Lys Arg
            100                 105                 110

(2) INFORMATION FOR SEQ ID NO: 37:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

Asp Ile Val Leu Thr Gln Ser Pro Ala Ser Leu Ala Val Ser Leu Gly
1               5                  10                  15

Gln Arg Ala Thr Ile Ser Cys Arg Ala Ser Glu Ser Val Asp Ser Tyr
                20                  25                  30

Gly Asn Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
        50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Leu Thr Phe Gly Ala Gly Thr Lys Leu Glu Leu Lys Arg
            100                 105                 110

(2) INFORMATION FOR SEQ ID NO: 38:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

Asp Ile Val Met Thr Gln Ser Ser Asn Ser Leu Ala Val Ser Leu Gly
1               5                  10                  15

Glu Arg Ala Thr Ile Asn Cys Lys Ser Ser Gln Ser Val Leu Tyr Ser
```

-continued

```
                    20                  25                  30
Ser Asn Ser Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Ser Phe Gly Gln Gly Thr Lys Leu Glu Ile
            100                 105                 110

Lys Arg
```